US009987321B2

(12) United States Patent
Christofidou-Solomidou et al.

(10) Patent No.: US 9,987,321 B2
(45) Date of Patent: Jun. 5, 2018

(54) USE OF FLAXSEED AND FLAXSEED DERIVATIVES FOR TREATMENT OF NEUROLOGICAL DISORDERS AND VIRAL DISEASES

(71) Applicant: The Trustees of the University of Pennsylvania, Philadelphia, PA (US)

(72) Inventors: Melpo Christofidou-Solomidou, Eagleville, PA (US); Kelly Jordan-Sciutto, Lansdale, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 337 days.

(21) Appl. No.: 14/083,804

(22) Filed: Nov. 19, 2013

(65) Prior Publication Data

US 2014/0308379 A1    Oct. 16, 2014

Related U.S. Application Data

(60) Provisional application No. 61/728,476, filed on Nov. 20, 2012, provisional application No. 61/789,986, filed on Mar. 15, 2013.

(51) Int. Cl.

| | |
|---|---|
| *A61K 36/55* | (2006.01) |
| *A61K 36/185* | (2006.01) |
| *A61K 31/70* | (2006.01) |
| *A61K 31/365* | (2006.01) |
| *A61K 31/05* | (2006.01) |

(52) U.S. Cl.
CPC .............. *A61K 36/55* (2013.01); *A61K 31/05* (2013.01); *A61K 31/365* (2013.01); *A61K 31/70* (2013.01)

(58) Field of Classification Search
None
See application file for complete search history.

(56) References Cited

U.S. PATENT DOCUMENTS

| | | | | |
|---|---|---|---|---|
| 6,004,559 A | * | 12/1999 | Sinnott | A61K 36/185 424/737 |
| 6,307,122 B1 | * | 10/2001 | Epstein | A01K 67/0271 424/93.1 |
| 6,486,126 B1 | * | 11/2002 | Prasad | A61K 31/74 424/78.08 |
| 7,582,786 B2 | * | 9/2009 | Malfroy-Camine | C07F 13/005 556/34 |

FOREIGN PATENT DOCUMENTS

| | | | | |
|---|---|---|---|---|
| CN | 101919457 A | * | 12/2010 | |
| WO | WO 03084974 A1 | * | 10/2003 | ............... C07H 1/08 |
| WO | WO 2009145839 A1 | * | 12/2009 | ............ C07C 237/06 |

OTHER PUBLICATIONS

The article of Hano et al. (The lignan (+)-secoisolariciresinol extracted from flax hulls is an effective protectant of linseed oil and its emulsion against oxidative damage, http://onlinelibrary.wiley.com/wol1/doi/10.1002/ejlt.201600219/full, published 2017).*
Eklund et al. Synthesis of (−)-matairesinol, (−)-enterolactone, and (−)-enterodiol from the natural lignan hydroxymatairesinol*Org. Lett.*, 2003, 5 (4), pp. 491-493.
Ma et al., "Antidepressant-like effect of flaxseed secoisolariciresinol diglycoside in ovariectomized mice subjected to unpredictable chronis stress", Metab. Brain Dis., 2013, 28(1): 77-84.
Hasiewicz-Derkacz et al., "Natural phenolics greatly increase flax (*Linum usitatissimum*) oil stability", BMC Biotechnology (2015) 15:62.
Goyal et al., "Flax and flaxseed oil: an ancient medicine & modern functional food", J Food Sci Technol (Sep. 2014) 51(9):1633-1653.
Michotte et al., "Linseed oil stabilisation with pure natural phenolic compounds", Food Chemistry 129 (2011) 1228-1231.
Thompson et al., "Flaxseed and its lignan and oil components reduce mammary tumor growth at a late stage of carcinogenesis", Carcinogenesis vol. 17 No. 6 pp. 1373-1376, 1996.
Saggar et al., "Dietary flaxseed lignan or oil combined with tamoxifen treatment affects MCF-7 tumor growth through estrogen receptor- and growth factor-signaling pathways", *Mol. Nutr. Food Res.* 2010, 54, 415-425.

* cited by examiner

*Primary Examiner* — Chris R Tate
*Assistant Examiner* — Randall Winston
(74) *Attorney, Agent, or Firm* — Mark S. Cohen; Pearl Cohen Zedek Latzer Baratz LLP

(57) ABSTRACT

The invention provides compositions and methods for treating neurological disorders and viral infection using wholegrain flaxseed, flaxseed lignans such as Secoisolariciresinol diglucoside (SDG), human lignans metabolized from flaxseed such as Enterodiol (ED) or Enterolactone (EL), and synthetic flaxseed lignan analogs.

8 Claims, 23 Drawing Sheets

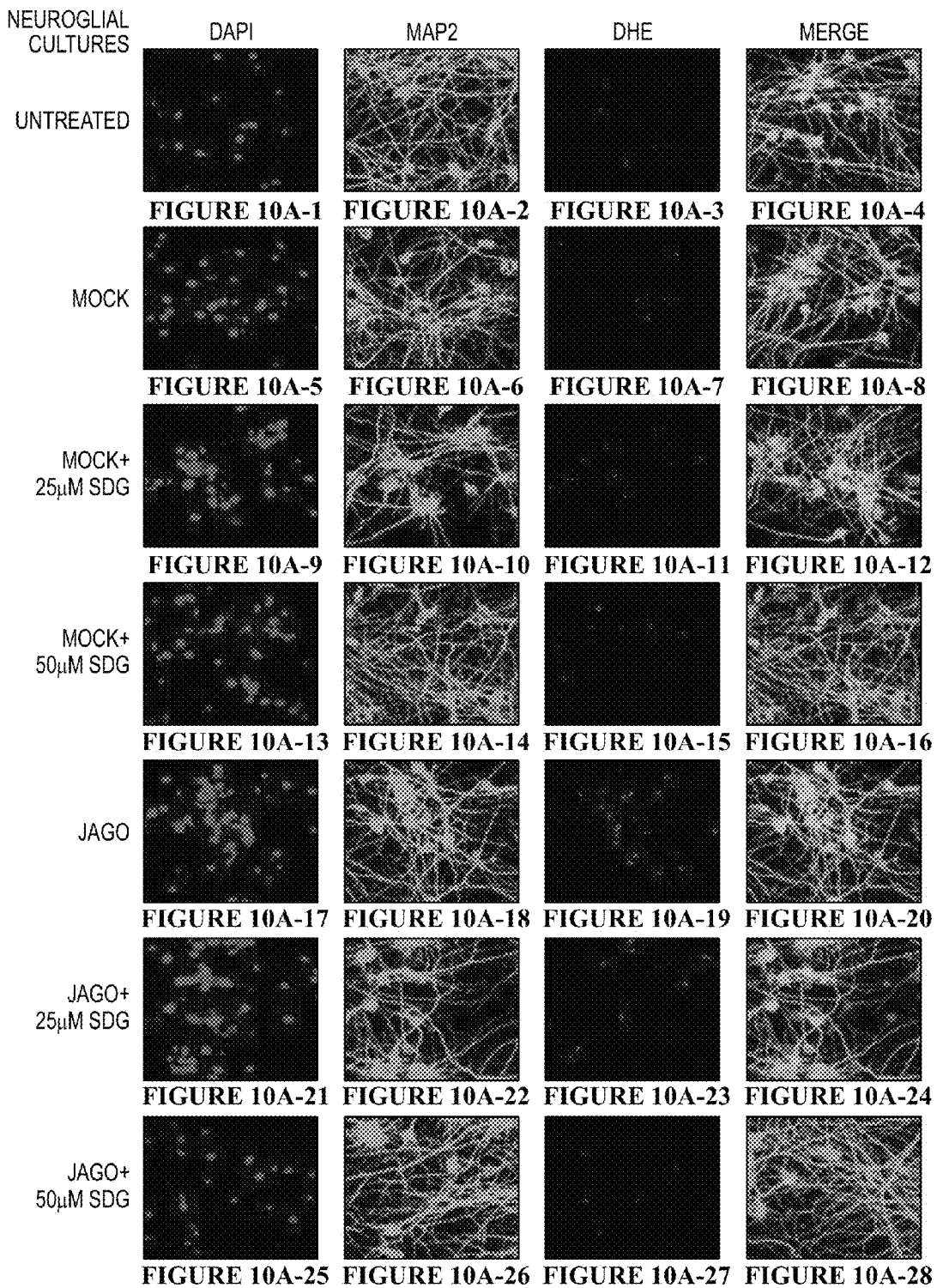

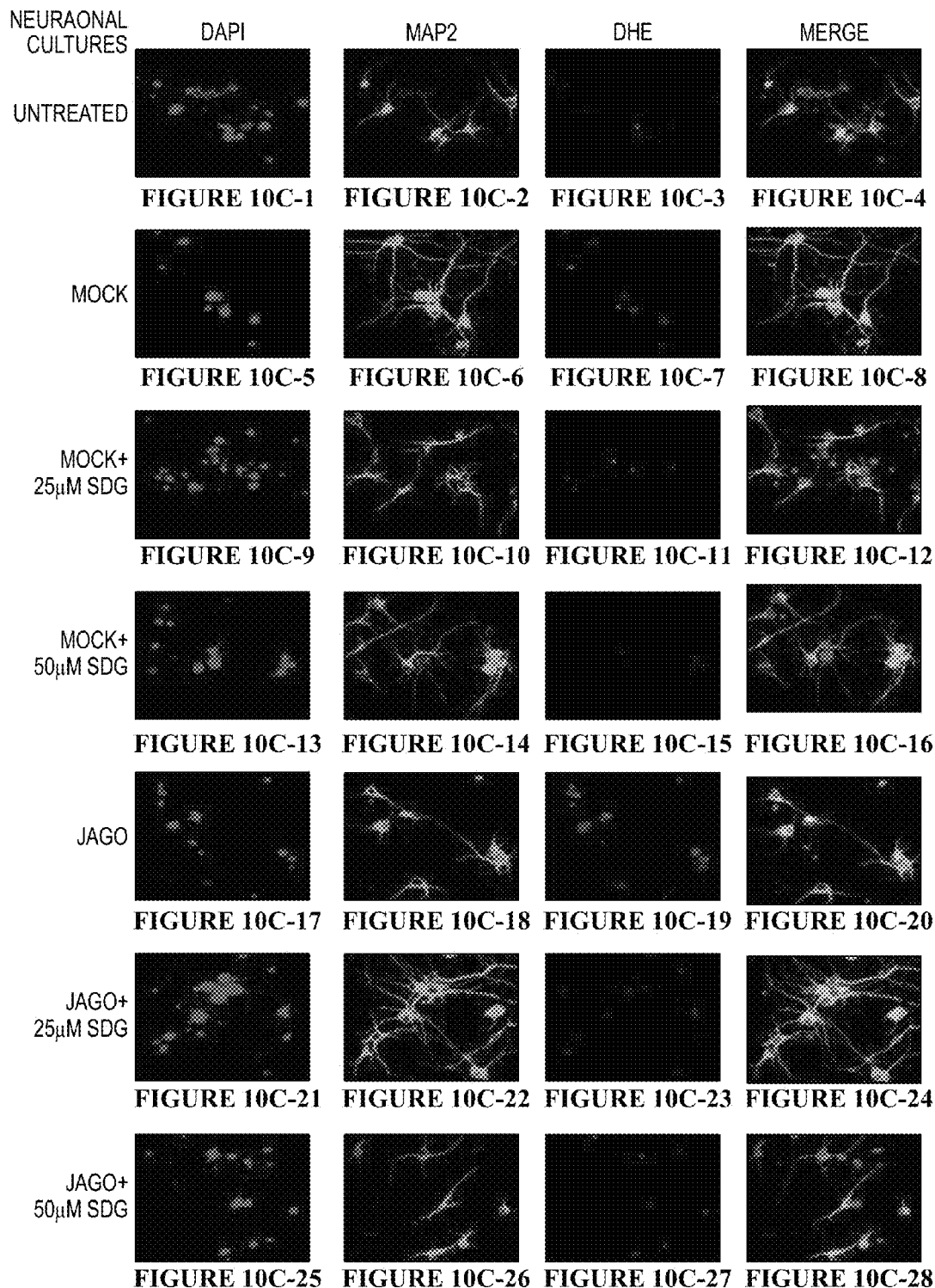

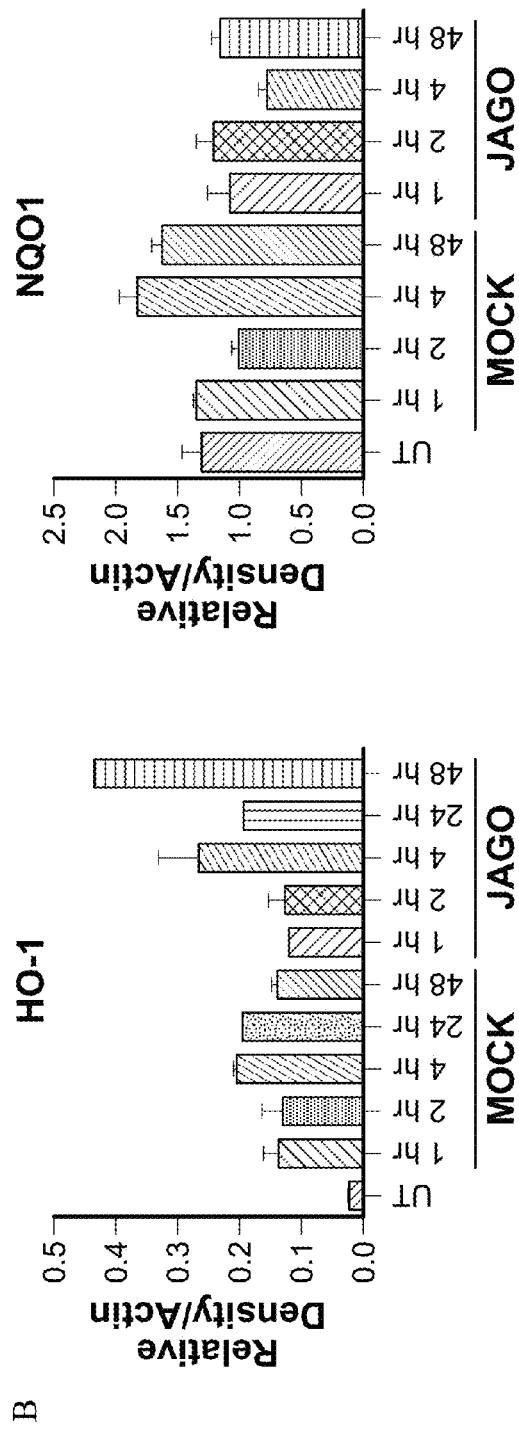
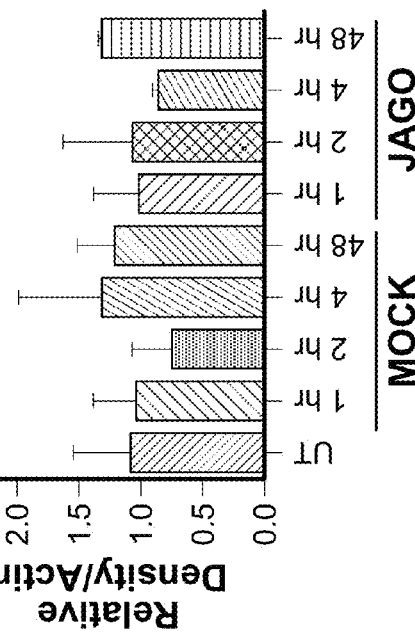
Figure 12B-1
Figure 12B-2
Figure 12B-3

USE OF FLAXSEED AND FLAXSEED DERIVATIVES FOR TREATMENT OF NEUROLOGICAL DISORDERS AND VIRAL DISEASES

CROSS-REFERENCE TO RELATED APPLICATIONS

This application claims priority to and benefit of U.S. Provisional Patent Applications 61/728,476 and 61/789,986, filed Nov. 20, 2012 and Mar. 15, 2013, respectively, both of which are incorporated by reference herein in their entirety.

FIELD OF THE INVENTION

Provided herein are compositions and methods for treating neurological disorders and viral infection using whole-grain flaxseed, flaxseed lignans such as Secoisolariciresinol diglucoside (SDG), human lignans metabolized from flaxseed such as Enterodiol (ED) or Enterolactone (EL), and synthetic flaxseed lignan analogs.

BACKGROUND OF THE INVENTION

The prevalence of HIV infection worldwide is greater than 40 million people; in the United States, over 1 million people are infected. HIV-associated neurocognitive disorders (HAND)—progressing in disability from asymptomatic neurocognitive impairment (ANI) to HIV-associated mild neurocognitive disorder (MND) to HIV-associated dementia (HAD)—has been recognized as common sequelae of infection. Early in the epidemic, more than 50% of all HIV-positive patients were diagnosed with HAD.

Thanks to the advent of antiretroviral therapy, human immunodeficiency virus (HIV)-infected individuals have significantly reduced mortality and morbidity. The prevalence of HAD has greatly diminished while less severe ANI and MND have risen as individuals live longer with the disease. However, HIV-infected individuals are dependent on the use of antiretroviral drugs to suppress HIV replication for the remainder of their lives. Several studies showed that nucleoside reverse transcriptase inhibitors, non-nucleoside reverse transcriptase inhibitors, and protease inhibitors induce overproduction of reactive oxygen species (ROS) associated with devastating side effects to the heart, liver, and central nervous system.

Also, emerging evidence indicates that persistence of HIV in patients treated with antiretroviral therapy and possibly the antiretroviral therapy itself contribute to cognitive decline such as seen in HAND as the HIV-infected population ages.

There is therefore a need in the art for adjunctive neuroprotective therapy in addition to antiretroviral therapy for treatment of cognitive decline as the HIV-infected individuals. Also, there is a need to inhibit viral infection or viral entry in to a cell.

Dietary flaxseed (FS) is a nutritional whole grain with high contents of omega-3 fatty acids and lignans. Flaxseed is the richest source of the lignan secoisolariciresinol diglucoside (SDG). After ingestion, secoisolariciresinol diglucoside (SDG) is converted to secoisolariciresinol, which is further metabolized by intestinal bacteria to the mammalian lignans enterodiol and enterolactone. Clinical studies using dietary SDG stress its safety and tolerability and showed that a dose of at least 500 mg SDG/day for approximately 8 weeks has a positive effect on cardiovascular risk factors in humans. Flaxseed can be safely consumed in adequate quantities to induce the anti-oxidant response pathway and to exert anti-inflammatory and free radical scavenging properties via the action of its polyphenolic lignan component, secoisolariciresinol diglucoside (SDG).

A growing body of evidence indicates that SDG metabolites may provide cardiovascular (CV) and anti-cancer benefits due to their weak oestrogenic or anti-oestrogenic effects, antioxidant activity, ability to induce phase 2 proteins and/or inhibit the activity of certain enzymes, or by other as yet unidentified mechanisms. SDG metabolites may protect against CV disease and the metabolic syndrome by reducing lipid and glucose concentrations, lowering blood pressure, and decreasing oxidative stress and inflammation. Flax lignans may also reduce cancer risk by preventing pre-cancerous cellular changes and by reducing angiogenesis and metastasis. Moreover, FS and SDG are protective in lungs against hyperoxia, acid aspiration, lipopolysaccharide-induced acute lung injury, warm lung ischemia/reperfusion injury and pneumonitis, resulting from thoracic radiation.

SUMMARY OF THE INVENTION

In one aspect, methods for treating neuronal damage in a subject are provided, the methods include: the step of administering to said subject a therapeutically effective amount of flaxseed, a bioactive component or a metabolite thereof, or an analog of said bioactive component or metabolite, thereby treating neuronal damage in said subject.

In another aspect, methods for treating a viral infection in a subject are provided, the methods include: the step of administering to said subject a therapeutically effective amount of flaxseed, a bioactive component or a metabolite thereof, or an analog of said bioactive component or metabolite, thereby treating said viral infection in said subject.

In an other aspect, methods of attenuating viral replication in a subject are provided, the methods include: the step of administering to said subject a therapeutically effective amount of flaxseed, a bioactive component or a metabolite thereof, or an analog of said bioactive component or metabolite, thereby attenuating viral replication in said subject In a further aspect, methods for mitigating the neurotoxic effects of an anti-retroviral therapy in a subject are provided, the methods include: the step of administering to said subject a therapeutically effective amount of flaxseed, a bioactive component or a metabolite thereof, or an analog of said bioactive component or metabolite, thereby mitigating said neurotoxic effects of said anti-retroviral therapy in said subject.

In an additional aspect, compositions for treating neuronal damage in a subject are provided, the compositions comprising: a therapeutically effective amount of flaxseed, or a bioactive component or a metabolite thereof, or an analog of said bioactive component or metabolite.

In yet another aspect, compositions for treating a viral infection in a subject are provided, the compositions comprising: a therapeutically effective amount of flaxseed, a bioactive component or a metabolite thereof, or an analog of said bioactive component or metabolite.

In yet another aspect, compositions for attenuating viral replication in a subject, the compositions comprising are provided: a therapeutically effective amount of flaxseed, a bioactive component or a metabolite thereof, or an analog of said bioactive component or metabolite.

In yet another aspect, provides compositions for mitigating the neurotoxic effects of an anti-retroviral therapy in a subject are provided, the compositions comprising: a therapeutically effective amount of flaxseed, a bioactive component or a metabolite thereof, or an analog of said bioactive component or metabolite.

In yet another aspect, methods for inhibiting the entry of a human immunodeficiency virus (HIV) into a cell of a subject are provided, the methods include: the step of administering to said subject a composition comprising a therapeutically effective amount of flaxseed, a bioactive component or a metabolite thereof, or an analog of said bioactive component or metabolite, thereby inhibiting the entry of said HIV into said cell of said subject.

In yet another aspect, methods for inhibiting the expression of a coreceptor associated with the entry of HIV into a cell of a subject are provided, the methods include: the step of administering to said subject a composition comprising a therapeutically effective amount of flaxseed, a bioactive component or a metabolite thereof, or an analog of said bioactive component or metabolite, wherein said coreceptor is C—C chemokine receptor type 5 (CCR5), C—X—C chemokine receptor type 4 (CXCR4), or a combination thereof, thereby inhibiting the expression of said coreceptor associated with the entry of said HIV, and thereby inhibiting the entry of said HIV into said cell of said subject.

In yet another aspect, methods for inhibiting the infection of HIV in a subject are provided, where said subject is at risk of the infection of said virus, the methods include: the step of administering to said subject a composition comprising a therapeutically effective amount of flaxseed, a bioactive component or a metabolite thereof, or an analog of said bioactive component or metabolite, thereby inhibiting the infection of said HIV in said subject.

In yet another aspect, methods for inhibiting the reinfection of HIV in a subject are provided, where said subject is at risk of the reinfection of said virus, the methods include: the step of administering to said subject a composition comprising a therapeutically effective amount of flaxseed, a bioactive component or a metabolite thereof, or an analog of said bioactive component or metabolite, thereby inhibiting the reinfection of said HIV in said subject.

Unless otherwise defined, all technical and scientific terms used herein have the same meaning as commonly understood by one of ordinary skill in the art to which this invention belongs. Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description. It is also contemplated that whenever appropriate, any embodiment of the present invention can be combined with one or more other embodiments of the present invention, even though the embodiments are described under different aspects of the present invention.

BRIEF DESCRIPTION OF THE DRAWINGS

FIG. 10 (C-1 to C-28, D) also shows that SDG reduces harmful/damaging free radical formation in neurons exposed to HIV (Jago).

DETAILED DESCRIPTION OF THE INVENTION

Figure 1:
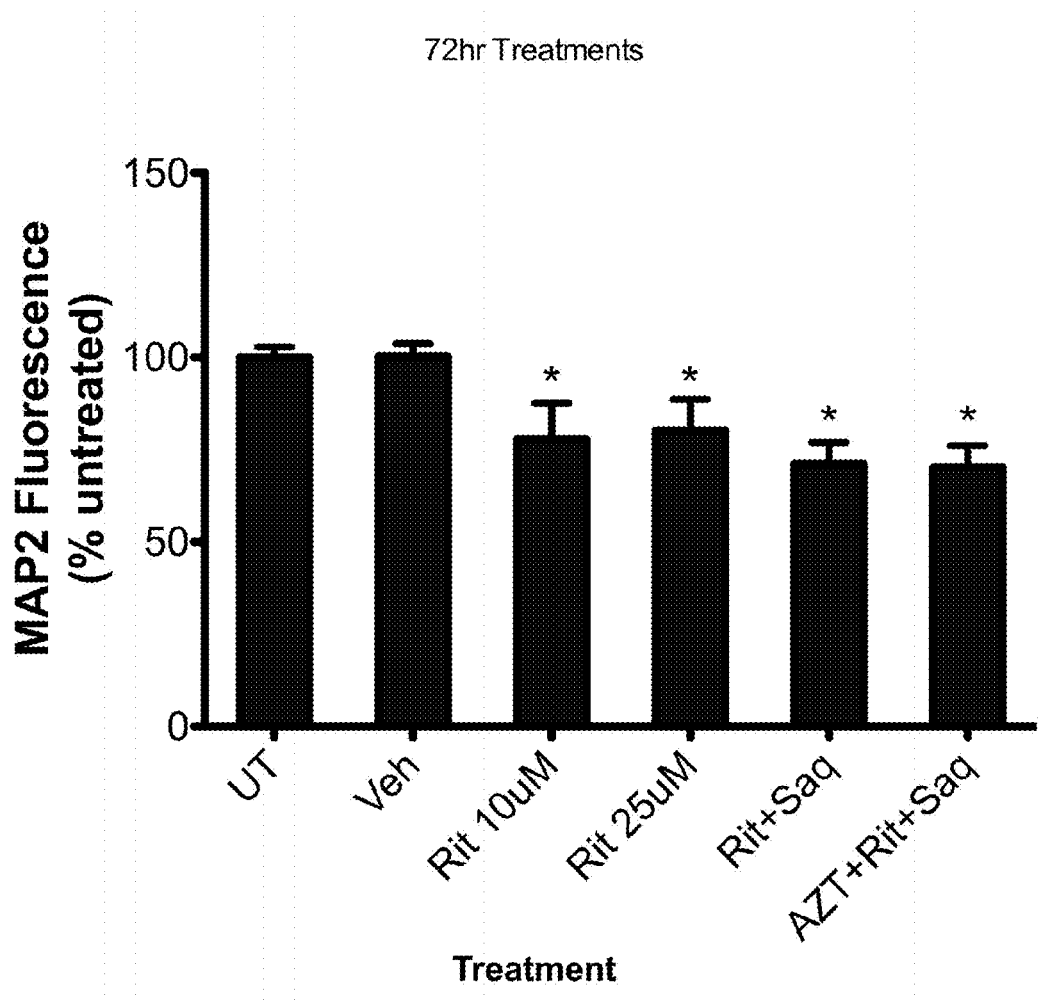
FIG. 1 shows that combination Antiretroviral Therapy (cART) induces Neuronal Damage. Relative neuronal damage as indicated by MAP2 cell-based ELISA in neurons treated with the indicated concentrations of ART compounds, ritonavir (RIT), Saquinavir (Sag), and Zidovudine (AZT). Cells were treated for 72 hours with ritonavir (10 μM or 25 μM), ritonavir (10 μM)+Saquinivir (1 μM), AZT (25 μM)+ritonavir+Saquinavir. One hour before and two hours after cART drug treatment, half of the wells of a 96 well plate of neuroglial cultures were also treated with secoisolariciresinol diglucoside (SDG) (25 μM, 50 μM, or 100 μM) where indicated. 72 hours later, a MAP2 cell-based ELISA assay was used to quantify neuronal death and damage. Untreated cultures in addition to vehicle (0.08% DMSO) treated cultures with and without SDG were used as controls. The value for untreated cultures was set to 100%, and SDG and cART treated bands are expressed as a percent change from untreated. Data represent the average±SEM counts of at least three biological replicates. *$p<0.0001$ vs UT.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Provided herein are therapeutic and prophylactics methods of use for flaxseed and its bioactive products, derivatives, ingredients, components, metabolites, extracts or combinations thereof, or an analog of said bioactive products, derivatives, ingredients, components, metabolites, extracts or combinations thereof.

In one aspect, methods for treating neuronal damage in a subject are provided, the methods include: the step of administering to said subject a therapeutically effective amount of flaxseed, a bioactive component or a metabolite thereof, or an analog of said bioactive component or metabolite, thereby treating neuronal damage in said subject.

In another aspect, methods for treating a viral infection in a subject are provided, the methods include: the step of administering to said subject a therapeutically effective amount of flaxseed, a bioactive component or a metabolite thereof, or an analog of said bioactive component or metabolite, thereby treating said viral infection in said subject.

In an other aspect, methods of attenuating viral replication in a subject are provided, the methods include: the step of administering to said subject a therapeutically effective amount of flaxseed, a bioactive component or a metabolite thereof, or an analog of said bioactive component or metabolite, thereby attenuating viral replication in said subject In a further aspect, methods for mitigating the neurotoxic effects of an anti-retroviral therapy in a subject are provided, the methods include: the step of administering to said subject a therapeutically effective amount of flaxseed, a bioactive component or a metabolite thereof, or an analog of said bioactive component or metabolite, thereby mitigating said neurotoxic effects of said anti-retroviral therapy in said subject.

In an additional aspect, compositions for treating neuronal damage in a subject are provided, the compositions comprising: a therapeutically effective amount of flaxseed, or a bioactive component or a metabolite thereof, or an analog of said bioactive component or metabolite.

In yet another aspect, compositions for treating a viral infection in a subject are provided, the compositions comprising: a therapeutically effective amount of flaxseed, a bioactive component or a metabolite thereof, or an analog of said bioactive component or metabolite.

In yet another aspect, compositions for attenuating viral replication in a subject, the compositions comprising are provided: a therapeutically effective amount of flaxseed, a bioactive component or a metabolite thereof, or an analog of said bioactive component or metabolite.

In yet another aspect, provides compositions for mitigating the neurotoxic effects of an anti-retroviral therapy in a subject are provided, the compositions comprising: a therapeutically effective amount of flaxseed, a bioactive component or a metabolite thereof, or an analog of said bioactive component or metabolite.

In yet another aspect, methods for inhibiting the entry of a human immunodeficiency virus (HIV) into a cell of a subject are provided, the methods include: the step of administering to said subject a composition comprising a therapeutically effective amount of flaxseed, a bioactive component or a metabolite thereof, or an analog of said bioactive component or metabolite, thereby inhibiting the entry of said HIV into said cell of said subject.

In yet another aspect, methods for inhibiting the expression of a coreceptor associated with the entry of HIV into a cell of a subject are provided, the methods include: the step of administering to said subject a composition comprising a therapeutically effective amount of flaxseed, a bioactive component or a metabolite thereof, or an analog of said bioactive component or metabolite, wherein said coreceptor is C—C chemokine receptor type 5 (CCR5), C—X—C chemokine receptor type 4 (CXCR4), or a combination thereof, thereby inhibiting the expression of said coreceptor associated with the entry of said HIV, and thereby inhibiting the entry of said HIV into said cell of said subject.

In yet another aspect, methods for inhibiting the infection of HIV in a subject are provided, where said subject is at risk of the infection of said virus, the methods include: the step of administering to said subject a composition comprising a therapeutically effective amount of flaxseed, a bioactive component or a metabolite thereof, or an analog of said bioactive component or metabolite, thereby inhibiting the infection of said HIV in said subject.

In yet another aspect, methods for inhibiting the reinfection of HIV in a subject are provided, where said subject is at risk of the reinfection of said virus, the methods include: the step of administering to said subject a composition comprising a therapeutically effective amount of flaxseed, a bioactive component or a metabolite thereof, or an analog of said bioactive component or metabolite, thereby inhibiting the reinfection of said HIV in said subject.

Flax is an annual plant that thrives in deep moist soils rich in sand, silt, and clay. The seeds in the flax plant are filled with flaxseed oil, sometimes called linseed oil. Flaxseeds are known as *Linum usitatissimum* with the species name meaning "most useful". The flax plant originated in Mesopotamia and first records of the culinary use of flaxseeds is from the times of ancient Greece. Flaxseed was first planted in North America with the arrival of the early colonists. In the 17th century, flax was first introduced and planted in Canada, the country that is currently the major producer.

Flax products are made from the seeds found inside the fruits. The seeds contain a high amount of the essential fatty acids (EFAs), alpha-linolenic acid (ALA), and linoleic acid. ALA is a precursor of eicosapentaenoic acid (EPA) and docosahexaenoic acid (DHA), which belong to omega-3 fatty acids. While EPA and DHA are found primarily in fish, ALA is mostly found in flaxseed oil and other vegetable oils. Omega-3 fatty acids help reduce inflammation and most omega-6 fatty acids tend to promote inflammation. Studies indicate that flaxseed oil and other omega-3 fatty acids may be helpful in treating a variety of inflammatory conditions, such autoimmune diseases such as systemic lupus erythematosus (SLE). Flaxseed (as opposed to flaxseed oil) is also a good source of phytoestrogens.

In addition to omega-3 fatty acids, flaxseed products also contain lignans. Lignans are widely occurring plant compounds and are closely related to lignin, which forms the woody component of trees and other plants. The lignans are characterized by their dimeric composition from cinnamic acids, and they are attracting increasing attention as a result of their pharmacological properties. Lignans are believed to have direct antioxidant properties and can inhibit lipid peroxidation in various tissues.

According to certain embodiments, the methods provided herein comprise the use of a flaxseed metabolite, such as a flaxseed lignan. For example, the flaxseed lignan is secoisolariciresinol diglucoside (SDG).

SDG, an antioxidant isolated from flaxseed, is metabolized in the human intestine to enterodiol (ED), and enterolactone (EL). Unlike ED and EL, SDG is not directly taken up by cells. The ex vivo antioxidant activities of these three lignans (SDG, EL and ED) were shown by specifically inhibiting linoleic acid lipid peroxidation, indicating direct hydroxyl radical scavenging activity. In addition, due to their ability to inhibit platelet activating factor (PAF), lignans may exert antioxidant activity by inhibiting ROS production by white blood cells. Thus, the methods provided herein include the use of a flaxseed metabolite, such as a mammalian lignan. The mammalian lignan may be an enterodiol, an enterolactone, a combination thereof or synthetic analogs thereof (See, e.g., Eklund et al. *Org. Lett.*, 2003, 5 (4), pp 491-493).

The primary lignan found in flaxseed is 2,3-bis(3-methoxy-4-hydroxybenzyl) butane-1,4-diol (secoisolariciresinol), which is stored as the conjugate secoisolariciresinol diglucoside (SDG) in its native state in the plant. Flaxseed contains levels of phytoestrogens which are generally 75-800 times greater than any other plant food. The plant lignan, catecholic nordihydroguaiaretic acid, is a potent antioxidant and may be used in the compositions and methods provided herein.

The flaxseed used in the compositions and methods provided herein may be whole grain flaxseed. Alternatively, the flaxseed used in the compositions and methods provided herein is a lignan complex, for example without limitation, the complex comprises: 32.9% SDG, 13.9% cinnamic acids, 11.8% protein, 10.0% 3-hydroxy-3-methyl glutaric acid, 3.5% fat, 3.3% moisture, and 1.0% ash.

The whole grain flaxseed or flaxseed lignan complex (FLC) that may be used in the methods and compositions provided herein for treating viral infection, for attenuating viral replication, for treating neuronal damage, for mitigating the neurotoxic effects of an anti-retroviral therapy, for inhibiting the entry of a virus into a cell, and for inhibiting the viral infection or reinfection in a subject comprises the plant lignan precursor, secolsolariciresinol diglucoside (SDG). In certain embodiments, the whole grain flaxseed or flaxseed lignan metabolite comprises the mammalian lignan enterodiol. In certain embodiments, the whole grain flaxseed or flaxseed lignan metabolite comprises enterolactone. In certain embodiments, the whole grain flaxseed or flaxseed lignan metabolite comprises synthetic analogs of SDG. In certain embodiments, the whole grain flaxseed or flaxseed lignan metabolite comprises a combination of the foregoing.

The bioactive flaxseed component or its metabolite(s) may activate a transcription factor which modulates expression of protective enzymes, thereby reducing inflammation and oxidative tissue injury, whereby the inflammation or oxidative neuronal tissue injury is the result of a viral infection or a result of anti-retroviral therapy (ART).

Without wishing to be bound by theory, administration of dietary FS reduces ROS generation by alveolar monocyte derived macrophages (MDMs) in response to oxidative burst. As MDMs are a major source of HIV-induced neurotoxicity, the ability of FS to reduce superoxide from a macrophage population protects against HIV-infected MDMs in the CNS, as well as in the periphery. Additionally, SDG targets oxidative stress and neuroinflammation via activation of the endogenous antioxidant response (EAR), which has the distinct advantage of acting via enzymatic processes as opposed to stoichiometric-acting free radical scavengers.

In one embodiment, the transcription factor which modulates expression of protective enzymes, which is activated by the administration of the compositions provided herein, which include the whole grain flaxseed or flaxseed lignan complex (FLC), used in the methods provided herein, is nuclear factor E2-related factor 2 (Nrf2).

In another embodiment, SDG has the ability to upregulate Phase II enzymes in cell culture and in whole animals through activation of Nrf2.

Nrf2 is a "master" antioxidant transcription factor regulating many endogenous antioxidant enzymes such as heme-oxygenase I, GST, NQO-I, acetyltransferase, sulfotransferase or their combination. The transcription factor Nrf2 binds to and activates a specific "antioxidant response element" (ARE) in the promoter region of detoxifying and anti-oxidant enzyme genes. Under homeostatic conditions Nrf2 is bound by a Keap1 protein, which keeps the complex in the cytoplasm. Electrophiles and reactive oxygen species liberate Nrf2 from Keap1 and induce the translocation and accumulation of Nrf2 in the nucleus. Once in the nucleus, binding of Nrf2 to the ARE drives the induction of a gene group that enhances the reducing potential against electrophiles and free radicals, and elevates cellular capacity for repair/removal of oxidatively damaged proteins.

Flaxseed lignans used in the compositions provided herein, for the methods provided herein, may act directly or indirectly, on Nrf2, inducing its translocation to the nucleus and in one embodiment, activating ARE-regulated transcription. In some instances, Nrf2 is required or sufficient to induce endogenous antioxidant enzyme (AOE) enhancement.

Accordingly, provided herein are methods of treating a viral infection, for attenuating viral replication, for treating neuronal damage, and for mitigating the neurotoxic effects of an anti-retroviral therapy in a subject comprising administering to said subject a composition comprising a whole grain flaxseed, a bioactive ingredient or a metabolite thereof, or an analog of said bioactive component or metabolite, whereby the bioactive flaxseed component, its metabolite(s), or a synthetic analog thereof, activates a transcription factor which modulates expression of protective enzymes, thereby reducing inflammation and oxidative tissue injury, wherein the protective enzyme is Glutathione-S-transferase, N-acetyl transferase or other Nrf2-modulated enzymes.

The methods provided herein may modulate the regulation of genes mediated by the Nrf2/ARE pathway.

In one embodiment, the endogenous antioxidant and drug detoxifying enzymes that lead to more effective chemoprevention using the methods provided herein, are glutathione S-transferase (GST), NAD(P)H:quinone oxidoreductasel (NQO-I), epoxide hydrolase, glutamylcysteine synthetase, UDP:glucuronosyl transferases other Phase II metabolizing enzymes or a combination thereof.

In certain embodiments, the methods of the present invention comprise increasing dietary intake of flaxseed lignan metabolites by the subject, thereby inhibiting proteasome activity. In another embodiment, the ubiquitin-proteasome pathway plays a critical role in the degradation of cellular proteins and cell cycle control. In another embodiment, mitotic processes are strictly regulated by cyclins and cyclin-dependent kinases which in turn are important substrates of the proteasomal degradation pathway.

A "bioactive" product, derivative, component, ingredient, or metabolite is one that has a biological effect or function. For example, it has one or more of the same biological effect as flaxseed. It will be appreciated that the bioactive component may be chemically synthesized.

A "metabolite" is a substance produced by metabolism or by a metabolic process. For example, a metabolite of SDG is EL or ED.

It will be appreciated by one skilled in the art that a metabolite may be a chemically synthesized equivalent of a natural metabolite. Equivalent may refer to a compound with the same amino acid sequence as a second compound. Additionally, equivalent may refer to a compound with the same structure as a second compound. Furthermore, equivalent may refer to a compound with a high homology to a second compound (e.g., more than 85%, 90%, 95%, or 98% homology) and maintaining the function of the second compound.

An "analog" is a compound, drug, or hormone whose structure is related to that of another compound, drug, or hormone. Generally, the chemical properties of the analog are similar to the parent compound. Preferably, the biological properties of the analog are similar to the parent compound. More preferably, both the biological and the chemical properties of the analog are similar to the parent compound. The analog may be a synthetic analog.

A "derivative" of flaxseed is a substance that is produced from flaxseed using one or more biological or chemical process.

An "ingredient" or "component" is an element or a constituent in a mixture or compound.

A "product" is a substance resulting from a chemical reaction.

An "extract" is a preparation containing an active principle or concentrated essence of a material, for example, from flaxseed.

Provided herein are methods for treating neuronal damage in a subject, the methods comprising: the step of administering to said subject a therapeutically effective amount of flaxseed, or a bioactive component or a metabolite thereof, or an analog of said bioactive component or metabolite, thereby treating neuronal damage in said subject. As demonstrated in Example 1, the neuronal damage may be determined by decreases in MAP2 levels.

Neuronal Diseases/Disorders

In certain aspects, flaxseed, or a bioactive component or a metabolite thereof as described herein can be used to treat patients suffering from neuronal damage, which may be a result of neurodegenerative diseases, and/or traumatic or mechanical injury to the central nervous system (CNS), spinal cord or peripheral nervous system (PNS).

Provided herein are methods for treating a neurodegenerative disease (e.g., a chronic neurodegenerative disease) in a subject, the methods comprising: the step of administering to said subject a therapeutically effective amount of flaxseed, or a bioactive component or a metabolite thereof, or an analog of said bioactive component or metabolite, or an analog of said bioactive component or metabolite, thereby treating said neurodegenerative disease in said subject.

Neurodegenerative disease typically involves reductions in the mass and volume of the human brain, which may be due to the atrophy and/or death of brain cells, which are far more profound than those in a healthy person that are attributable to aging. Neurodegenerative diseases can evolve gradually, after a long period of normal brain function, due to progressive degeneration (e.g., nerve cell dysfunction and death) of specific brain regions. Alternatively, neurodegenerative diseases can have a quick onset, such as those associated with trauma or toxins. The actual onset of brain degeneration may precede clinical expression by many years. Examples of neurodegenerative diseases include, but are not limited to, Alzheimer's disease (AD), Parkinson's disease (PD), Huntington's disease (HD), Multiple Sclerosis (MS), amyotrophic lateral sclerosis (ALS; Lou Gehrig's disease), diffuse Lewy body disease, chorea-acanthocytosis, primary lateral sclerosis, ocular diseases (ocular neuritis), chemotherapy-induced neuropathies (e.g., from vincristine, paclitaxel, bortezomib), spinal muscular atrophy, diabetes-induced neuropathies and Friedreich's ataxia. Flaxseed, or a bioactive component or a metabolite thereof can be used to treat these disorders.

Flaxseed, or a bioactive component or a metabolite thereof as described herein can be used to treat patients suffering from glycolipid storage diseases caused by the lack of lysosomal β-hexosaminidase such as Tay-Sachs disease and Sandhoff disease. In either disorder, GM2 ganglioside and related glycolipids substrates for β-hexosaminidase accumulate in the nervous system and trigger acute neurodegeneration. In the most severe forms, the onset of symptoms begins in early infancy. A precipitous neurodegenerative course then ensues, with affected infants exhibiting motor dysfunction, seizure, visual loss, and deafness. Death usually occurs by 2-5 years of age.

Flaxseed, or a bioactive component or a metabolite thereof as described herein can be used to treat patients suffering from a peripheral neuropathy. The term "peripheral neuropathy" encompasses a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used.

Peripheral neuropathy may be a result of diabetes or leprosy, caused by the bacterium *Mycobacterium leprae*, which attacks the peripheral nerves of affected people. Peripheral neuropathy may also be a result of acrylamide poisoning or an inherited disorder.

A peripheral neuropathy may also be related to human immunodeficiency virus (HIV) infection. There are four main peripheral neuropathies associated with HIV, namely sensory neuropathy, AIDP/CIPD, drug-induced neuropathy and CMV-related.

The most common type of neuropathy associated with AIDS is distal symmetrical polyneuropathy (DSPN). This syndrome is a result of nerve degeneration and is characterized by numbness and a sensation of pins and needles. DSPN causes few serious abnormalities and mostly results in numbness or tingling of the feet and slowed reflexes at the ankles. It generally occurs with more severe immunosuppression and is steadily progressive. Treatment with tricyclic antidepressants relieves symptoms but does not affect the underlying nerve damage.

A less frequent, but more severe type of neuropathy is known as acute or chronic inflammatory demyelinating polyneuropathy (AIDP/CIDP). In AIDP/CIDP there is damage to the fatty membrane covering the nerve impulses. This kind of neuropathy involves inflammation and resembles the muscle deterioration often identified with long-term use of AZT. It can be the first manifestation of HIV infection, where the patient may not complain of pain, but fails to respond to standard reflex tests. This kind of neuropathy may be associated with seroconversion, in which case it can sometimes resolve spontaneously. It can serve as a sign of HIV infection and indicate that it might be time to consider antiviral therapy. AIDP/CIDP may be auto-immune in origin.

Drug-induced, or toxic, neuropathies can be very painful. Antiviral drugs commonly cause peripheral neuropathy, as do other drugs e.g. vincristine, dilantin (an anti-seizure medication), high-dose vitamins, isoniazid, and folic acid antagonists. Peripheral neuropathy is often used in clinical trials for antivirals as a dose-limiting side effect, which means that more drugs should not be administered. Additionally, the use of such drugs can exacerbate otherwise minor neuropathies. Usually, these drug-induced neuropathies are reversible with the discontinuation of the drug.

CMV causes several neurological syndromes in AIDS, including encephalitis, myelitis, and polyradiculopathy.

Furthermore, flaxseed, or a bioactive component or a metabolite thereof may be used to treat or prevent other peripheral neuropathies, such as Guillain-Barré syndrome, which may arise from complications associated with viral illnesses, such as cytomegalovirus, Epstein-Ban virus, and human immunodeficiency virus (HIV), or bacterial infection, including *Campylobacter jejuni* and Lyme disease.

Flaxseed, or a bioactive component or a metabolite thereof may be used to treat or prevent chemotherapeutic induced neuropathy. The flaxseed, or a bioactive component or a metabolite thereof may be administered prior to administration of the chemotherapeutic agent, concurrently with administration of the chemotherapeutic drug, and/or after initiation of administration of the chemotherapeutic drug. If the flaxseed, or a bioactive component or a metabolite thereof is administered after the initiation of administration of the chemotherapeutic drug, then preferably the flaxseed, or a bioactive component or a metabolite thereof be administered prior to, or at the first signs, of chemotherapeutic induced neuropathy.

The chemotherapy drugs which are most commonly associated with neuropathy, are the *Vinca* alkaloids (anti-cancer drugs originally derived from a member of the periwinkle—the *Vinca* plant genus) and a platinum-containing drug called Cisplatin. The *Vinca* alkaloids include the drugs vinblastine, vincristine and vindesine. Many combination chemotherapy treatments for lymphoma for example CHOP and CVP contain vincristine, which is the drug known to cause this problem most frequently. Indeed, it is the risk of neuropathy that limits the dose of vincristine that can be administered.

Also provided herein are methods for treating or preventing neuropathy related to ischemic injuries or diseases, such as, for example, coronary heart disease (including congestive heart failure and myocardial infarctions), stroke, emphysema, hemorrhagic shock, peripheral vascular disease (upper and lower extremities) and transplant related injuries.

The ischemic condition may result from a disorder that occurs in a part of the subject's body outside of the central nervous system, but yet still causes a reduction in blood flow to the central nervous system. These disorders may include, but are not limited to a peripheral vascular disorder, a venous thrombosis, a pulmonary embolus, arrhythmia (e.g. atrial fibrillation), a myocardial infarction, a transient ischemic attack, unstable angina, or sickle cell anemia. Moreover, the central nervous system ischemic condition may occur as result of the subject undergoing a surgical procedure.

Flaxseed, or a bioactive component or a metabolite thereof may be used to treat or prevent neuronal loss due to prion disease, in which neuronal loss is a salient feature. Prion diseases include Creutzfeldt-Jakob disease in human, BSE in cattle (mad cow disease), Scrapie Disease in sheep and goats, and feline spongiform encephalopathy (FSE) in cats.

In one embodiment, a combination drug regimen may include drugs or compounds for the treatment or prevention of neurodegenerative disorders or secondary conditions associated with these conditions. Thus, a combination drug regimen may include one or more flaxseed, or a bioactive component or a metabolite thereof and one or more anti-neurodegeneration agents. For example, one or more flaxseed, or a bioactive component or a metabolite thereof can be combined with an effective amount of one or more of: L-DOPA; a dopamine agonist; an adenosine A2A receptor antagonist; a COMT inhibitor; a MAO inhibitor; an N—NOS inhibitor; a sodium channel antagonist; a selective N-methyl D-aspartate (NMDA) receptor antagonist; an AMPA/kainate receptor antagonist; a calcium channel antagonist; a GABA-A receptor agonist; an acetyl-choline esterase inhibitor; a matrix metalloprotease inhibitor; a PARP inhibitor; an inhibitor of p38 MAP kinase or c-jun-N-terminal kinases; TPA; NDA antagonists; beta-interferons; growth factors; glutamate inhibitors; and/or as part of a cell therapy.

HIV-Associated Neurocognitive Disorder (HAND)

Provided herein are methods for mitigating the neurotoxic effects of an anti-retroviral therapy in a subject, the methods comprising: the step of administering to said subject a therapeutically effective amount of flaxseed, or a bioactive component or a metabolite thereof, or an analog of said bioactive component or metabolite, thereby mitigating said neurotoxic effects of said anti-retroviral therapy in said subject.

The term "mitigating" as used herein, in the context of an anti-retroviral therapy, describes rectifying, reversing, decreasing, or alleviating the adverse effects of an anti-retroviral therapy in a subject.

In one embodiment, the present invention provides methods for treating, treating neuronal damage in a subject with HIV-associated Neurocognitive Disorder (HAND).

HAND is characterized by a triad of cognitive, behavioral, and motor dysfunctions. For milder forms of HAND, such as asymptomatic neurocognitive impairment (ANI) or mild neurocognitive disorder (MND), mild difficulties in concentration, attention, and memory may be present while the neurologic examination is unremarkable. Patients complain of reading difficulties due to poor concentration levels. Affected individuals are easily distracted, lose their train of thought, and require repeated prompting. Activities of daily living may take longer and become more laborious. More severe forms of HAND, such as HIV-associated dementia (HAD), entail cognitive and motor dysfunctions that are more pronounced, with assistance of a caregiver required for maintaining activities of daily living. The most commonly observed symptoms include delayed speech output with long pauses between words, poor thought and emotional content characterized by lack of spontaneity, and social withdrawal often mistakenly diagnosed as severe depression. Gait abnormalities and a reduction in motor movements are observed. On neurologic examination, frontal release signs, spasticity, and brisk deep tendon reflexes are often present.

The compositions and methods provided herein may act on neurons to decrease neuronal damage. The compositions and methods provided herein may act on glia to decrease neuronal damage. The compositions and methods provided herein may act on microglia to decrease neuronal damage. The compositions and methods provided herein may reverse dendritic or synaptic damage in the brain.

HAND may be diagnosed using a combination of neuropsychological (NP) testing, neuroimaging studies, cerebrospinal fluid (CSF) analysis, where the results may support or refute other diagnoses. As is known to the skilled artisan, NP testing comprises testing of verbal/language, attention/working memory, abstraction/executive, memory (learning and recall), speed of information processing, motor skills, or a combination thereof. As is known to the skilled artisan, neuroimaging studies may include magnetic resonance imaging (MRI) studies, such as structural MRI or functional MRI.

The compositions and methods provided herein may exert their prophylactic or therapeutic effects by reducing chemokines, cytokines, or other inflammatory mediators in the brain.

The compositions and methods provided herein may exert their prophylactic or therapeutic effects in the brain. The compositions and methods provided herein may exert their effects on central white matter, frontal cortex, basal ganglia, thalamus, brain stem, or a combination thereof.

Although combination antiretroviral therapy (cART) reduces the viral load, low-level replication may still cause dysfunction of nerve cells through an ongoing inflammatory response and astrocytic gliosis. Viral proteins can stimulate brain microglia to produce excess amounts of chemokines, cytokines, and other inflammatory mediators. Typically, these factors regulate cell interactions and are important for normal cellular functioning. However, at higher concentrations, these inflammatory mediators cause neuronal dysfunction and death.

Thus, a subject in need of the treatment methods and/or compositions or kits described herein may be HIV-infected and receiving antiretroviral therapy. Alternatively, a subject in need of the treatment methods and/or compositions or kits described herein may be HIV-infected and not receiving antiretroviral therapy.

Antiretroviral therapy comprises treatment with a single anti-retroviral drug (monotherapy). Alternatively, antiretroviral therapy comprises treatment with multiple anti-retroviral drugs, such as combination anti-retroviral therapy (cART) or highly active antiretroviral therapy (HAART).

An antiretroviral drug may be an entry inhibitor or fusion inhibitor, such as, Maraviroc, enfuvirtide, or a combination thereof.

In some embodiments, an antiretroviral drug is a CCR5 receptor antagonist which binds to the CCR5 receptor on the surface of the T-Cell and block viral attachment to the cell.

In some embodiments, an antiretroviral drug is a nucleoside and nucleotide reverse transcriptase inhibitor (NRTI), which inhibits reverse transcription and/or results in DNA chain termination.

In some embodiments, an antiretroviral drug is a non-nucleoside reverse transcriptase inhibitor (NNRTI), which inhibits reverse transcriptase directly by binding to the enzyme and interfering with its function.

In some embodiments, an antiretroviral drug is a protease inhibitor (PI), which targets viral assembly by inhibiting the activity of protease, an enzyme used by HIV to cleave nascent proteins for the final assembly of new virons.

An antiretroviral drug may be an integrase inhibitor (e.g., raltegravir), which inhibits the enzyme integrase, which is responsible for integration of viral DNA into the DNA of the infected cell.

An antiretroviral drug may be a maturation inhibitor, which inhibits the last step in gag processing in which the viral capsid polyprotein is cleaved, thereby blocking the conversion of the polyprotein into the mature capsid protein (p24), resulting in non-infectious virions. Maturation inhibitors include, but are not limited to, alpha interferon, bevirimat, Vivecon, or a combination thereof.

The antiretroviral drug combination may be emtricitabine, tenofovir (both NRTI) and efavirenz (a NNRTI). The compositions and methods provided herein may be the antiretroviral drug combination is emtricitabine, tenofovir and raltegravir (an integrase inhibitor). In some embodiments, the antiretroviral drug combination is emtricitabine, tenofovir, ritonavir and darunavir (the latter two are protease inhibitors The antiretroviral drug combination may emtricitabine, tenofovir, ritonavir and atazanavir (the latter two are protease inhibitors).

In some embodiments, the antiretroviral drug combination is Combivir (available from GlaxoSmithKline), which is a combination of zidovudine and lamivudine. In some embodiments, the antiretroviral drug combination is Trizivir (available from GlaxoSmithKline), which is a combination of abacavir, zidovudine, and lamivudine. In some embodiments, the antiretroviral drug combination is Kaletra (available from Abbott Laboratories), which is a combination of lopinavir and ritonavir. In some embodiments, the antiretroviral drug combination is Epzicom (in USA) or Kivexa (in Europe) (available from GlaxoSmithKline), which a combination of abacavir and lamivudine. In some embodiments, the antiretroviral drug combination is Truvada (available from Gilead Sciences), which is a combination of emtricitabine and tenofovir. In some embodiments, the antiretroviral drug combination is Atripla (available from Gilead Sciences and Bristol-Myers Squibb), which is a combination of efavirenz, emtricitabine, and tenofovir. In one embodiment, a subject administered any of the above-listed drugs given as a monotherapy may also be treated according to the methods of the present invention.

Immune Reconstitution Inflammatory Syndrome (IRIS)

Provided herein are methods for treating IRIS in a subject, the methods comprising administering to said subject a therapeutically effective amount of flaxseed, its bioactive ingredient, or a metabolite thereof.

IRIS is a pathologic inflammatory reaction that occurs shortly after initiation of combination anti-retroviral therapy (cART). IRIS is due to an abrupt increase in immune surveillance, most notable when the compromise is quite severe, and response to therapy brisk. IRIS leads to a paradoxic clinical deterioration as individuals can have a worsening of manifestations of underlying infection or an unmasking of a subclinical infection as CD4 counts rise and HIV RNA VL drops. IRIS can result in clinically significant morbidity and mortality due to multiple organ involvement including the brain.

A flaxseed lignan for use in the compositions and methods of the present invention may be a glycoside of secoisolariciresinol, such as secoisolariciresinol diglucoside (SDG). In some embodiments, the flaxseed lignan is matairesinol, isolariciresinol, pinoresinol, syringaresinol, lariciresinol, hydroxymatairesinol, or a combination thereof.

In some embodiments, the flaxseed lignan is a synthetic flaxseed lignan. In some embodiments, the flaxseed lignan is a synthetic flaxseed lignan analog.

Provided herein are methods for mitigating the neurotoxic effects of an anti-retroviral therapy in a subject comprising the step of administering to said subject a therapeutically effective amount of flaxseed, its bioactive ingredient, or a metabolite thereof, thereby mitigating said neurotoxic effects of said anti-retroviral therapy in said subject. In some embodiments, the subject has HIV. In some embodiments, the subject has a retroviral infection, such as a Alpharetrovirus (e.g., an Avian leukosis virus or Rous sarcoma virus). In some embodiments, the retroviral infection is a Betaretrovirus infection (e.g., Mouse mammary tumour virus or a human analogue thereof). In some embodiments, the retroviral infection is a Gammaretrovirus infection (e.g., a Murine leukemia virus, Feline leukemia virus or a human analogue thereof). In some embodiments, the retroviral infection is a Deltaretrovirus infection (e.g., a Bovine leukemia virus or a Human T-lymphotropic virus). In some embodiments, the retroviral infection is an Epsilonretrovirus infection (e.g., a Walleye dermal sarcoma virus). In some embodiments, the retroviral infection is a Lentivirus infection (e.g., Human immunodeficiency virus 1, Simian immunodeficiency virus, or Feline immunodeficiency virus). In some embodiments, the retroviral infection is a Spumavirus infection (e.g., a Simian foamy virus).

Provided herein are methods for treating a pathogenic infection in a subject comprising the step of administering to said subject a therapeutically effective amount of flaxseed, or a bioactive component or a metabolite thereof, or an analog of said bioactive component or metabolite, thereby treating said pathogenic infection in said subject. Also provided herein are methods for treating a viral infection in a subject, the methods include: the step of administering to said subject a therapeutically effective amount of flaxseed, or a bioactive component or a metabolite thereof, or an analog of said bioactive component or metabolite, thereby treating said viral infection in said subject. Also provided herein are methods for attenuating viral replication in a subject, the methods include: the step of administering to said subject a therapeutically effective amount of flaxseed, or a bioactive component or a metabolite thereof, or an analog of said bioactive component or metabolite, thereby attenuating viral replication in said subject.

Pathogenic Infections

In some embodiments, the viral pathogenic effect, infection, or combination thereof is mediated by any one or more of the following pathogens: hepatitis B virus, hepatitis C virus, human immunodeficiency virus, human herpesviruses, herpes simplex virus-1, herpes simplex virus-2, human cytomegalovirus, Epstein-Ban virus, Varicella-Zoster virus, human herpesvirus-6, human herpesvirus-7, human influenza, measles virus, hantaan virus, pneumonia virus, rhinovirs, poliovirus, human respiratory syncytial virus, retrovirus, human T-cell leukemia virus, rabies virus, mumps virus, malaria (*Plasmodium falciparum*), *Bordetelia pertussis, Diptheria, Rickettsia prowazekii, Borrelia bergdorferi*, Ebola virus. In some embodiments, the viral pathogenic effect, infection or combination thereof is mediated by Pichinde virus, while in other embodiments, it is mediated by Punta Toro virus.

In some embodiments, the pathogenic effect, infection or combination thereof is mediated by one or more of the following pathogens: Helminths, *Bacillus anthracis* (anthrax), *Clostridium botulinum, Yersinia pestis, Variola major* (smallpox) and other pox viruses, *Francisella tularensis* (tularemia), Arenaviruses, Lymphocytic choriomeningitis, Junin virus, Machupo virus, Guanarito virus, Lassa Fever, Bunyaviruses, Hantaviruses, Rift Valley Fever, Flaviruses, Dengue, Filoviruses, Ebola, Marburg, hemorrhagic fever viruses, Tickborne hemorrhagic fever viruses, Crimean-Congo Hemorrhagic fever virus, Tickborne encephalitis viruses, Yellow fever, Tuberculosis, Multi-drug resistant tuberculosis, Influenza, *Rickettsias*, Rabies virus, Severe acute respiratory syndrome-associated coronavirus (SARS), *Burkholderia pseudomallei, Coxiella burnetii* (Q fever), *Brucella* species (brucellosis), *Burkholderia mallei* (glanders), Ricin toxin (from *Ricinus communis*), Epsilon toxin of *Clostridium perfringens, Staphylococcus* enterotoxin B, Typhus fever (*Rickettsia prowazekii*), Diarrheagenic *E. coli*, Pathogenic Vibrios, *Shigella* species, *Salmonella, Listeria monocytogenes, Campylobacter jejuni, Yersinia enterocolitica*), Caliciviruses, Hepatitis A, *Cryptosporidium parvum, Cyclospora cayatanensis, Giardia lamblia, Entamoeba histolytica, Toxoplasma*, Microsporidia, West Nile Virus, LaCrosse, California encephalitis, Western Equine Encephalitis, Eastern Equine Encephalitis, Venezuelan Equine Encephalitis, Japanese Encephalitis Virus, and Kyasanur Forest Virus.

In some embodiments, the pathogenic effect, infection, or combination thereof is mediated by one or more of the following microorganisms: *Actinobacillus pleuropneumoniae, Aeropyrum pernix, Agrobacterium tumeficians, Anopheles gambiae, Aquifex aeolicus, Arabidopsis thaliana, Archeglobus fulgidis, Bacillus anthracis, bacillus cereus, Baccilus halodurans, Bacillus subtilis, Bacteroides thetaiotaomicron, Bdellovibrio bacteriovorus, Bifidobacterium longum, Bordetella bronchiseptica, Bordetella pertussis, Borrelia burgdorferi, Bradyrhizobium japonicum, Brucella melitensis, Brucella suis, Bruchnera aphidicola, Brugia malayi, Caenorhabditis elegans, Canipylobacter jejuni, Candidatus blochmanniafloridanus, Caulobacter crescentus, Chlorobium tepidum, Chromobacterium violaceum, Clostridium acetobutylicum, Clostridium perfringens, Clostridium tetani, Corynebacterium diphtheriae, Corynebacterium efficiens, Corynebacterium glutamicum, Coxiella burnetii, Danio rerio, Dechloromonas aromatica, Deinococcus radiodurans, Drosophila melanogaster, Eimeria tenella, Eimeria acervulina, Entamoeba histolytica, Enterococcus faecalis, Escherichia coli, Fusobacterium nucleatum, Geobacter su6rurreducens, Gloeobacter violaceus, Haemophilis ducreyi, Haemophilus influenzae, Halobacterium, Helicobacter hepaticus, Helicobacter pylori, Lactobacillus johnsonii, Lactobacillus plantarum, Lactococcus lactis, Leptospira interrogans serovar lai, Listeria innocua, Listeria monocytogenes, Mesorhizobium loti, Methanobacter thermoautotrophicus, Methanocaldocossus jannaschii, Methanococcoides burtonii, Methanopyrus kandleri, Methanosarcina acetivorans, Methanosareina mazei God, Mycobacterium avium, Mycobacterium bovis, Mycobacterium leprae, Mycobacterium tuberculosis, Mycoplasma gallisepticum strain R, Mycoplasma genitalium, Mycoplasma penetrans, Mycoplasma pneumoniae, Mycoplasma pulmonis, Nanoarchaeum equitans, Neisseria meningitidis, Nitrosomonas europaea, Nostoc, Oceanobacillus iheyensis, Onion yellows phytoplasma, Oryzias latipes, Oryza sativa, Pasteurella multocida, Photorhabdus luminescens, Pirellula, Plasmodium falciparum, Plasmodium vivax, Plasmodium yoelii, Porphyromonas gingivalis, Prochlorococcus marinus, Pseudomonas aeruginosa, Pseudomonas putida, Pseudomonas syringae, Pyrobaculum aerophilum, Pyrococcus abyssi, Pyrococcus furiosus, Pyrococcus horikoshii, Ralstonia solanacearum, Rhodopseudomonas palustris, Rickettsia conorii, Rickettsia prowazekii, Rickettsia rickettsii, Saccharomyces cerevisiae, Salmonella enterica, Salmonella typhimurium, Sarcocystis cruzi, Schistosoma mansoni, Schizosaccharomyces pombe, Shewanella oneidensis, Shigella flexneri, Sinorhizobium meliloti, Staphylococcus aureus, Staphylococcus epidermidis, Streptococcus agalactiae, Streptococcus agalactiae, Streptococcus mutans, Streptococcus pneumoniae, Streptococcus pyogenes, Streptomyces avermitilis, Streptomyces coelicolor, Suffiblobus tokodaii, Synechocystis sp., Takifugu rubripes, Tetraodon fluviatilis, Theileria parva, Thermoanaerobacter tengcongensis, Thermoplasma acidophilum, Thermoplasma voleanium, Thermosynechococcus elongatus, Aermotoga maritima, Toxoplasma gondii, Treponema denticola, Treponema pallidum, Tropheryma whipplei, Tryponosoma brucei, Trypanosoma cruzi, Ureaplasma urealyticum, Vibrio cholerae, Vibro parahaemolyticus, Pbro vulnificus, Wigglesworthia brevipalpis, Wolbachia endosymbiont of Drosophilia melanogaster, WOlinella succinogenes, Xanthomonas axonopodis* pv. *Citri, Xanthomonas campestris* pv. *Campestris, Xylella fastidiosa,* or *Yersinia pestis*.

In some embodiments, the pathogenic effect, infection or combination thereof is mediated by a parasite. In one embodiment, the parasite is a worm. In some embodiments, the parasitic worm is a helminth, Acanthocephala, *Clonorchis sinensis* (the Chinese liver fluke), Dracunculiasis (Guinea Worm Disease), or *Enterobius vermicularis* (pinworm). In some embodiments, the parasite is a fish (e.g., a Candiru (Vampire fish of Brazil)). In some embodiments, the parasite is a fungi (e.g., a Tinea (ringworm)). In some embodiments, the parasite is a protist (e.g., a *Plasmodium* (malaria), *Balantidium coli,* or *Giardia lamblia*). In some embodiments, the parasite is Hirudinea (leech), Phthiraptera (lice), Siphonaptera (fleas), or Acarina (ticks).

In some embodiments, the parasite is an intracellular bacterial parasite. In one embodiment, the intracellular bacterial parasite is *Rickettsias,* while in another embodiment, its *Mycobacterium leprae*. In one embodiment, the intracellular bacterial parasite is *Rickettsia prowazekii,* while in another embodiment, its *Rickettsia rickettsii* (Rocky mountain spotted fever).

In some embodiments, the methods provided herein may be used to treat a pathogenic infection acquired via zoonotic transmission. In some embodiments, the methods provided herein may be used to treat pathogenic infections acquired from avian, swine, bovine, or bat. In some embodiments, the methods provided herein may be used to treat Menangle, Hendra, Australian Bat Lyssavirus, Nipah, or Tioman. In some embodiments, the methods provided herein may be used to diminish pathogen reservoirs in animal species. In some embodiments, the methods provided herein may be used to treat a human infected with a pathogen.

HIV

In some embodiments, the compositions and methods provided herein are for the prevention or treatment of a pathogenic infection. In some embodiments, the pathogenic infection is viral. In some embodiments, the viral pathogenic effect described herein is mediated by Human Immunodeficiency Virus (HIV). Thus, in some embodiments, a subject in need of the treatment methods and/or compositions described herein is HIV-infected. In some embodiments, a subject in need of the treatment methods and/or compositions described herein is at the risk of HIV-infection. In some embodiments, a subject in need of the treatment methods and/or compositions described herein had been exposed to HIV virus. In some embodiments, a subject in need of the treatment methods and/or compositions described herein is receiving antiretroviral therapy. In some embodiments, a subject in need of the treatment methods and/or compositions described herein is diagnosed with an HIV-associated Neurocognitive Disorder (HAND).

C—C chemokine receptor type 5 (CCR5) and C—X—C chemokine receptor type 4 (CXCR4) are the two major coreceptors for HIV entry into cells. CXCR4 (also known as fusin) is expressed on T cells. Co-expression of CXCR4 and CD4 on a cell allow T-tropic HIV isolates to fuse with and infect the cell. HIV gp120 interacts with both CD4 and CXCR4 to adhere to the cell and to effect conformational changes in the 120/gp41 complex that allow membrane fusion by gp41.

CCR5 is expressed on macrophages and on some populations of T cells, can also function in concert with CD4 to allow HIV membrane fusion. HIV gp120 binding to CCR5 is CD4-dependent. M-tropic HIV isolates use CCR5 as their coreceptor for infection both of macrophages and of some T cells.

In one embodiment, provided herein are methods for inhibiting the expression of a coreceptor associated with the entry of HIV into a cell of a subject. The coreceptor is CCR5, CXCR4, or a combination thereof. The methods include: the step of administering to said subject a composition comprising a therapeutically effective amount of flaxseed, a bioactive component or a metabolite thereof, or an analog of said bioactive component or metabolite, thereby inhibiting the expression of said coreceptor associated with the entry of said HIV, and thereby inhibiting the entry of said HIV into said cell of said subject.

In another embodiment, provided herein are methods for inhibiting the infection of HIV in a subject, said subject at the risk of the infection of said virus. In another embodiment, provided herein are methods for inhibiting the reinfection of HIV in a subject, said subject at the risk of the reinfection of said virus. The methods include: the step of administering to said subject a composition comprising a therapeutically effective amount of flaxseed, a bioactive component or a metabolite thereof, or an analog of said bioactive component or metabolite, thereby inhibiting the infection or reinfection of said HIV in said subject.

In some embodiments, methods of treating infection comprise treating a macrophage-tropic strain of HIV, T cell-tropic strain of HIV, or any combination thereof. In some embodiments, the compositions provided herein treat infections mediated by a macrophage-tropic strain of HIV. In other embodiments, the compositions treat infections mediated by a T cell-tropic strain of HIV. In some embodiments, the compositions treat infections mediated by either a macrophage-tropic strain of HIV, a T cell-tropic, or both. In some embodiments, the mechanisms of action of the compositions for use in the present invention differ based on the tropism of HIV.

In some embodiments, the methods provided herein comprise treating secondary complications of HIV infection. In some embodiments, the methods provided herein comprise treating opportunistic infections, neoplasms, neurologic abnormalities, or progressive immunologic deterioration. In some embodiments, the methods provided herein comprise treating acquired immunodeficiency syndrome. In some embodiments, the methods provided herein comprise treating a decline in the number of $CD4^+$ T lymphocytes.

In some embodiments, methods of treating infection comprise treating Clade A, B, C, D, A/E, F, G, H, J, or K. In some embodiments, the viral pathogenic effect, infection or combination thereof is mediated by HIV-1, while in other embodiments, they are mediated by HIV-2. In some embodiments, they are mediated by the M group of HIV-1, in other embodiments, they are mediated by the O group of HIV-1, while in yet other embodiments, they are mediated by the N group of HIV-1. In some embodiments, they are mediated by the A clade (or subtype) of the M group of HIV-1, in other embodiments, they are mediated by the B clade of the M group of HIV-1, in other embodiments, they are mediated by the C clade of the M group of HIV-1, in other embodiments, they are mediated by the D clade of the M group of HIV-1, in other embodiments, they are mediated by the A/E clade of the M group of HIV-1, in other embodiments, they are mediated by the F clade of the M group of HIV-1, in other embodiments, they are mediated by the G clade of the M group of HIV-1, in other embodiments, they are mediated by the H clade of the M group of HIV-1, in other embodiments, they are mediated by the J clade of the M group of HIV-1, in other embodiments, they are mediated by the K clade of the M group of HIV-1, in other embodiments, they are mediated by the A/G/I clade of the M group of HIV-1, while in other embodiments, they are mediated by a circulating recombinant form (CRF) of any of the above clades.

Treatment of Viral Encephalitis

Provided herein are methods for treating a viral infection in a subject comprising the step of administering to said subject a therapeutically effective amount of flaxseed, or a bioactive component or a metabolite thereof, or an analog of said bioactive component or metabolite, thereby treating said viral infection in said subject, wherein said virus is a viral encephalitide.

Infection of the central nervous system (CNS) by viruses is an uncommon event, considering the overwhelming number of individuals affected by the different human viral infections. Most commonly, clinically relevant viral encephalitis affects children, young adults, or elderly patients, but the spectrum of involvement depends on the specific viral agent, host immune status, and genetic and environmental factors.

The term "acute viral encephalitis" (from Greek enkephalos+-itis, meaning brain inflammation) is used to describe restricted CNS involvement (i.e., involvement of the brain, sparing the meninges); however, most CNS viral infections involve the meninges to a greater or lesser extent, leading to aseptic meningitis or causing mild meningoencephalitis rather than pure encephalitis.

In addition to acute viral encephalitis, other less established and more unusual manifestations of viral infections include progressive neurologic disorders, such as postinfectious encephalomyelitis (such as may occur after measles or Nipah virus encephalitis) and conditions such as postpoliomyelitis syndrome, which has been considered by some to be as a persistent manifestation of poliovirus infection. The compositions for use in the present invention also provide methods of treating any of the above encephalitises.

In some embodiments, the viral encephalitis is Herpes Simplex Encephalitis, California Encephalitis, Eastern Equine Encephalitis, Japanese Encephalitis, St Louis Encephalitis, Venezuelan Encephalitis, Western Equine Encephalitis, or West Nile Encephalitis.

In some embodiments, compositions and methods provided herein treat, prevent, inhibit, or suppress neuronal damage in a subject. In some embodiments, neuronal damage is inhibited by 50% compared to a) prior to treatment, b) untreated controls c) placebo-treated controls or d) subjects treated with another therapeutic composition. In some embodiments, neuronal damage is inhibited by 60%. In some embodiments, neuronal damage is inhibited by 70%. In some embodiments, neuronal damage is inhibited by 80%. In some embodiments, neuronal damage is inhibited by 90%. In some embodiments, neuronal damage is inhibited by 95%. In another embodiment, neuronal damage is inhibited by about 100%.

In some embodiments, compositions and methods provided herein mitigate the neurotoxic effects of anti-retroviral therapy in a subject. As used herein, "neurotoxic effects" or "neurotoxicity" describes adverse effects on the structure or function of the central and/or peripheral nervous system caused by exposure to a toxic chemical. Such adverse affects include, include but are not limited to, muscle weakness, loss of sensation and motor control, tremors, cognitive alterations, and autonomic nervous system dysfunction.

In some embodiments, neurotoxicity is inhibited by 50% compared to a) prior to treatment, b) untreated controls c) placebo-treated controls or d) subjects treated with another therapeutic composition. In some embodiments, neurotoxicity is inhibited by 60%. In some embodiments, neurotoxicity is inhibited by 70%. In some embodiments, neurotoxicity is inhibited by 80%. In some embodiments, neurotoxicity is inhibited by 90%. In some embodiments, neurotoxicity is inhibited by 95%. In some embodiments, neurotoxicity is inhibited by about 100%.

Compositions

Provided herein are compositions for carrying out the methods described herein. Provided herein are compositions for treating neuronal damage in a subject, the compositions comprising a therapeutically effective amount of flaxseed, or a bioactive component or a metabolite thereof, or an analog of said bioactive component or metabolite. Provided herein are compositions for treating a viral infection in a subject, the compositions comprising a therapeutically effective amount of flaxseed, or a bioactive component or a metabolite thereof, or an analog of said bioactive component or metabolite. Provided herein are compositions for attenuating viral replication in a subject, the compositions comprising a therapeutically effective amount of flaxseed, or a bioactive component or a metabolite thereof, or an analog of said bioactive component or metabolite. Provided herein are compositions for mitigating the neurotoxic effects of an anti-retroviral therapy in a subject, the compositions comprising a therapeutically effective amount of flaxseed, or a bioactive component or a metabolite thereof, or an analog of said bioactive component or metabolite.

Kits

In addition, provided herein are kits for preventing, inhibiting or suppressing neuronal damage in a subject comprising a therapeutically effective amount of flaxseed, or a bioactive component or a metabolite thereof, or an analog of said bioactive component or metabolite, and instructions for use thereof.

In another embodiment, provided herein are kits for treating a viral infection in a subject, the kits include a therapeutically effective amount of flaxseed, or a bioactive component or a metabolite thereof, or an analog of said bioactive component or metabolite, and instructions for use thereof.

In another embodiment, provided herein are kits for attenuating viral replication in a subject, the kits include a therapeutically effective amount of flaxseed, or a bioactive component or a metabolite thereof, or an analog of said bioactive component or metabolite, and instructions for use thereof.

In another embodiment provided herein are kits for mitigating the neurotoxic effects of an anti-retroviral therapy in a subject, the kits include a therapeutically effective amount of flaxseed, or a bioactive component or a metabolite thereof, or an analog of said bioactive component or metabolite, and instructions for use thereof.

Provided herein are kits for carrying out the methods provided herein as described herein. Accordingly, a variety of kits are provided. The kits may be used for any one or more of the following (and, accordingly, may contain instructions for any one or more of the following uses): reducing severity of a symptom of a viral infection in an individual at risk of being exposed to, exposed to or infected by a virus; suppressing infection in an individual at risk of being exposed to, exposed to or infected by a virus; preventing a symptom of a viral infection in an individual at risk of being exposed to, exposed to or infected by a virus; delaying development of a symptom of a viral infection in an individual at risk of being exposed to, exposed to or infected by a virus; reducing duration of a viral infection in an individual at risk of being exposed to, exposed to or infected by a virus. As is understood in the art, any one or more of these uses would be included in instructions directed to treating or preventing a viral infection.

The kits described herein comprise one or more containers comprising a flaxseed, its bioactive ingredient, or a metabolite thereof, and a set of instructions, generally written instructions although electronic storage media (e.g., magnetic diskette or optical disk) containing instructions are also acceptable, relating to the use and dosage of the flaxseed, its bioactive ingredient, or a metabolite thereof for the intended treatment. The instructions included with the kit generally include information as to dosage, dosing schedule, and route of administration for the intended treatment. The containers of flaxseed, its bioactive ingredient, or a metabolite thereof may be unit doses, bulk packages (e.g., multi-dose vials) or sub-unit doses.

The flaxseed, its bioactive ingredient, or a metabolite thereof component of the kit may be packaged in any convenient, appropriate packaging. For example, if the flaxseed is a freeze-dried formulation, a vial with a resilient stopper is normally used, so that the drug may be easily reconstituted by injecting fluid through the resilient stopper. Ampoules with non-resilient, removable closures (e.g., sealed glass) or with resilient stoppers are most conveniently used for injectable forms of a bioactive flaxseed ingredient or metabolite. Also, prefilled syringes may be used when the kit is supplied with a liquid formulation of the bioactive flaxseed ingredient or metabolite. The kit may contain the bioactive flaxseed ingredient, metabolite, or synthetic lignan analog in an ointment for topical formulation in appropriate packaging. Also contemplated are packages for use in combination with a specific device, such as an inhaler, nasal administration device (e.g., an atomizer) or an infusion device such as a minipump or transdermal administration device.

In some embodiments, the flaxseed is present in the kit as part of a food product (e.g., is bread, a muffin, a cookie, or a nutrition bar).

In some embodiments, the flaxseed is stored in whole grain form under cold storage, and ground and packaged in daily dose (e.g., 30 g) sealed opaque packets as needed. In some embodiments, the flaxseed is ground, or the hull split, in order to enhance the absorption of its omega-3 fatty acids and lignans). In some embodiments, starter kits with stepped doses are provided. For example, for days 1-3, packets contain only 10 g of ground flaxseed, for days 4-6 packets contain 20 g of flaxseed, and by day 7 the full 30 g dose is provided. This stepped dose approach can be useful given the considerable fiber load that flaxseed imposes on the gut (~9 g/30 g dose), and the propensity for gastrointestinal discomfort if initiated in full-dose fashion. Subjects receiving flaxseed are also instructed to drink at least 64 oz. of fluids/day to reduce any potential risk of colonic impaction or dehydration resulting from the increased fiber load, and to keep their flaxseed packets under refrigeration (to reduce spoilage).

Pharmaceutical Compositions and Methods of Administration

In some embodiments, the methods provided herein comprise administering a pharmaceutical composition comprising the flaxseed, its bioactive ingredient, a synthetic lignan analog, or a metabolite thereof and a pharmaceutically acceptable carrier.

"Pharmaceutical composition" refers to a therapeutically effective amount of the active ingredient, e.g., the flaxseed, its bioactive ingredient, a synthetic lignan analog, or a metabolite thereof, together with a pharmaceutically acceptable carrier or diluent. A "therapeutically effective amount" refers to that amount which provides a therapeutic effect for a given condition and administration regimen.

The pharmaceutical compositions containing the flaxseed, its bioactive ingredient, a synthetic lignan analog, or a metabolite thereof can be administered to a subject by any method known to a person skilled in the art, such as orally, parenterally, transmucosally, transdermally, intramuscularly, intravenously, intra-dermally, subcutaneously, intra-peritonealy, intra-ventricularly, intra-cranially, intra-vaginally or intra-tumorally.

In some embodiments, the pharmaceutical compositions are administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like. In some embodiments, the active ingredient is formulated in a capsule. In accordance with this embodiment, the compositions of the present invention comprise, in addition to the active compound and the inert carrier or diluent, a hard gelating capsule.

In some embodiments, compositions provided herein comprising bioactive flaxseed components are administered to a patient orally. In some embodiments, the oral administration is via increasing dietary intake of flaxseed or of other natural products comprising SDG, or a synthetic analog. In some embodiments, the oral administration is via administering a diet comprising a therapeutic amount of a composition comprising bioactive flaxseed components.

In some embodiments, the pharmaceutical compositions are administered by intravenous, intra-arterial, or intra-muscular injection of a liquid preparation. Suitable liquid formulations include solutions, suspensions, dispersions, emulsions, oils and the like. In some embodiments, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In some embodiments, the pharmaceutical compositions are administered intra-muscularly and are thus formulated in a form suitable for intra-muscular administration.

In some embodiments, the pharmaceutical compositions are administered topically to body surfaces and are thus formulated in a form suitable for topical administration. Suitable topical formulations include gels, ointments, creams, lotions, drops and the like. For topical administration, the flaxseed, its bioactive ingredient, or a metabolite thereof is prepared and applied as a solution, suspension, or emulsion in a physiologically acceptable diluent with or without a pharmaceutical carrier.

In some embodiments, the pharmaceutical compositions provided herein are controlled-release compositions, i.e. compositions in which the flaxseed, its bioactive ingredient, or a metabolite thereof is released over a period of time after administration. Controlled- or sustained-release compositions include formulation in lipophilic depots (e.g. fatty acids, waxes, oils). In other embodiments, the composition is an immediate-release composition, i.e. a composition in which all the flaxseed, its bioactive ingredient, or a metabolite thereof is released immediately after administration.

In some embodiments, compositions for use in the methods provided herein are administered at a therapeutic dose once per day. In some embodiments, the compositions are administered once every two days, twice a week, once a week, or once every two weeks.

In some embodiments, whole grain flaxseed is administered to a subject. In some embodiments, ground flaxseed is administered to a subject.

In some embodiments, whole grain flaxseed or ground flaxseed is administered at a dose of approximately 20.0 to 50.0 g. In one embodiment, whole grain flaxseed or ground flaxseed is administered at a dose of approximately 38 g. In some embodiments, whole grain flaxseed or ground flaxseed is administered at a dose of approximately 25 g. In some embodiments, whole grain flaxseed or ground flaxseed is administered at a dose of approximately 10 to 75 g. In some embodiments, whole grain flaxseed or ground flaxseed is administered at a dose of approximately 30 to 40 g. In some embodiments, whole grain flaxseed or ground flaxseed is administered at a dose of approximately 30 to 35 g. In some embodiments, whole grain flaxseed or ground flaxseed is administered at a dose of approximately 25 to 45 g. In some embodiments, whole grain flaxseed or ground flaxseed is administered at a dose of approximately 35 to 40 g. 10 grams of flaxseed is approximately 1 tablespoon of flaxseed.

In some embodiments, purified or synthetic SDG or synthetic SDG analog is administered to a subject in need thereof. A technique for extracting and purifying SDG is known in the art and described in U.S. Pat. No. 5,705,618, which is incorporated herein by reference. In some embodiments, it is desirable to treat subjects with SDG, especially if large amounts of SDG are needed, because only about 30-45 g of flaxseed should be consumed on a daily basis without side effects such as increased Taxation, believed due to the presence of a mucilaginous substance, and also to progressive weight gain resulting from the rather high caloric value of the oil component. Flax contains upwards of 40% oil. The use of whole ground flaxseed or meal is also less desirable in part because of the presence of cyanogenic glycosides present in the seed.

In some embodiments, bioactive components for use in the methods and kits provided herein are chemically synthesized directly into the mammalian, readily metabolizable forms, Enterodiol (ED) or Enterolactone (EL), as is known in the art.

In some embodiments, SDG is administered at a dose of 5-100 mg/kg. In some embodiments, SDG is administered at a dose of 5-50 mg/kg. In some embodiments, SDG is administered at a dose of 5-25 mg/kg. In some embodiments, SDG is administered at a dose of 10-15 mg/kg. In some embodiments, SDG is administered at a dose of 25-75 mg/kg. In some embodiments, SDG is administered at a dose of about 44 mg/kg. In some embodiments, SDG is administered at a dose of about 22 mg/kg. In some embodiments, SDG is administered at a dose of 50 mg/kg. In some embodiments, SDG is administered at a dose of approximately 500 mg/day.

In some embodiments, a flaxseed lignan is administered to a subject. In some embodiments, a flaxseed lignan is administered at a dose of 200 to 600 mg per subject. In some embodiments, a flaxseed lignan is administered at a dose of about 430 mg per subject.

In some embodiments, the treatment with flaxseed or a bioactive component or a metabolite thereof is for at least about 2 to 52 weeks. In some embodiments, the treatment is for at least about 8.5 weeks. In some embodiments, the treatment is for at least about 32 to 39 days.

In some embodiments, any of the compositions for use in the present invention will comprise flaxseed, or a bioactive component or a metabolite thereof, in any form or embodiment as described herein. In some embodiments, any of the compositions for use in this invention will consist of a flaxseed, or a bioactive component or a metabolite thereof, in any form or embodiment as described herein. In some embodiments, of the compositions for use in this invention will consist essentially of flaxseed, or a bioactive component or a metabolite thereof, in any form or embodiment as described herein. As used herein, the term "comprise" refers to the inclusion of the indicated active agent, such as the flaxseed, or a bioactive component or a metabolite thereof, as well as the inclusion of other active agents, and pharmaceutically acceptable carriers, excipients, emollients, stabilizers, etc., as are known in the pharmaceutical and nutraceutical industries. As used herein, the term "consisting essentially of" with refers to a composition, whose only active ingredient is the indicated active ingredient (e.g., flaxseed, or a bioactive component or a metabolite thereof). However, other compounds may be included which are for stabilizing, preserving, etc. the formulation, but are not involved directly in the therapeutic effect of the indicated active ingredient. As used herein, the term "consisting essentially of" may also allow for the inclusion of components which facilitate the release of the active ingredient. As used herein, the term "consisting" refers to a composition, which contains the active ingredient and a pharmaceutically acceptable carrier or excipient.

As used herein, "treating" may refer to either therapeutic treatment or prophylactic or preventative measures, wherein the object is to prevent or lessen the targeted pathologic condition or disorder as described hereinabove, or both. Therefore, compositions for use in the methods provided herein may be administered to/contacted with a subject before exposure to HIV or before the development of HAND. In some cases, compositions for use in the methods provided herein may be administered to/contacted with a subject after exposure to HIV or after the development of HAND. Thus treating a condition as described herein may refer to preventing, inhibiting, or suppressing the condition in a subject.

Furthermore, as used herein, the terms "treat" and "treatment" refer to therapeutic treatment, as well prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment. Those in need of treatment include those already with the disease or condition as well as those prone to having the disease or condition or those in which the disease or condition is to be prevented.

In some embodiments, symptoms are primary, while in other embodiments, symptoms are secondary. As used herein, "primary" refers to a symptom that is a direct result of the disease or disorder, while, "secondary" refers to a symptom that is derived from or consequent to a primary cause. The compositions and provided herein treat primary or secondary symptoms or secondary complications related to the disease or disorder.

As used herein, "symptoms" may be any manifestation of the disease or disorder, for example, HIV.

As used herein, "subject" refers to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The term "about" or "approximately" means within an acceptable error range for the particular value as determined by one of ordinary skill in the art, which will depend in part on how the value is measured or determined, i.e., the limitations of the measurement system.

The following examples are presented in order to more fully illustrate the preferred embodiments of the invention. They should in no way be construed, however, as limiting the broad scope of the invention.

Example 1

Neuroprotective Effects of Flaxseed Lignan SDG

Materials and Methods

Cells were treated for 72 hours with ritonavir (10 μM or 25 μM), ritonavir (10 μM)+Saquinivir (1 μM), AZT (25 μM)+ritonavir+Saquinavir. One hour before and two hours after cART drug treatment, half of the wells of a 96 well plate of neuroglial cultures were also treated with SDG (25 μM, 50 μM, or 100 μM). 72 hours later, a MAP2 cell-based ELISA assay was used to quantify neuronal death and damage. Untreated cultures in addition to vehicle (0.08% DMSO) treated cultures with and without SDG were used as controls. The value for untreated cultures was set to 100%, and SDG and cART treated bands are expressed as a percent change from untreated.

Results

Figure 3:
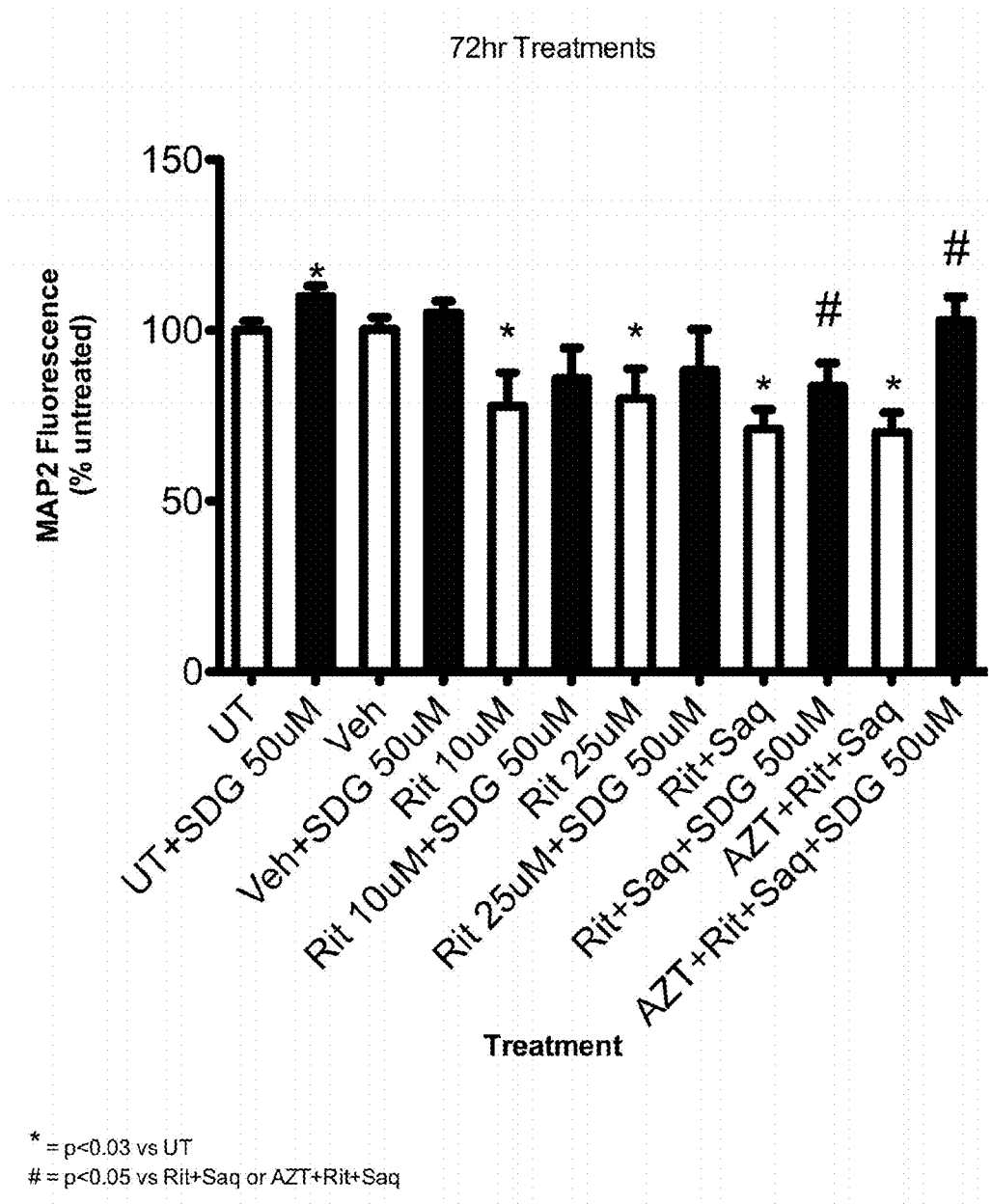
FIG. 3 shows that the Flaxseed Lignan Secoisolariciresinol Diglucoside (SDG) attenuates cART-mediated neurotoxicity. Relative neuronal damage as indicated by MAP2 cell-based ELISA with or without 25 μM SDG. Cells were treated for 72 hours with ritonavir (10 μM or 25 μM), ritonavir (10 μM)+Saquinivir (1 μM), AZT (25 μM)+ritonavir+Saquinavir. One hour before and two hours after cART drug treatment, half of the wells of a 96 well plate of neuroglial cultures were also treated with SDG (25 μM, 50 μM or 100 μM) where indicated. 72 hours later, a MAP2 cell-based ELISA assay was used to quantify neuronal death and damage. Untreated cultures in addition to vehicle (0.08% DMSO) treated cultures with and without SDG were used as controls. The value for untreated cultures was set to 100%, and SDG and cART treated bands are expressed as a percent change from untreated. Data represent the average±SEM counts of at least three biological replicates. *$p<0.0001$ vs UT, #$p<0.0005$ vs UT or Rit+Saq, $$p<0.05$ vs AZT+ritonavir+Saquinavir.
Figure 4:
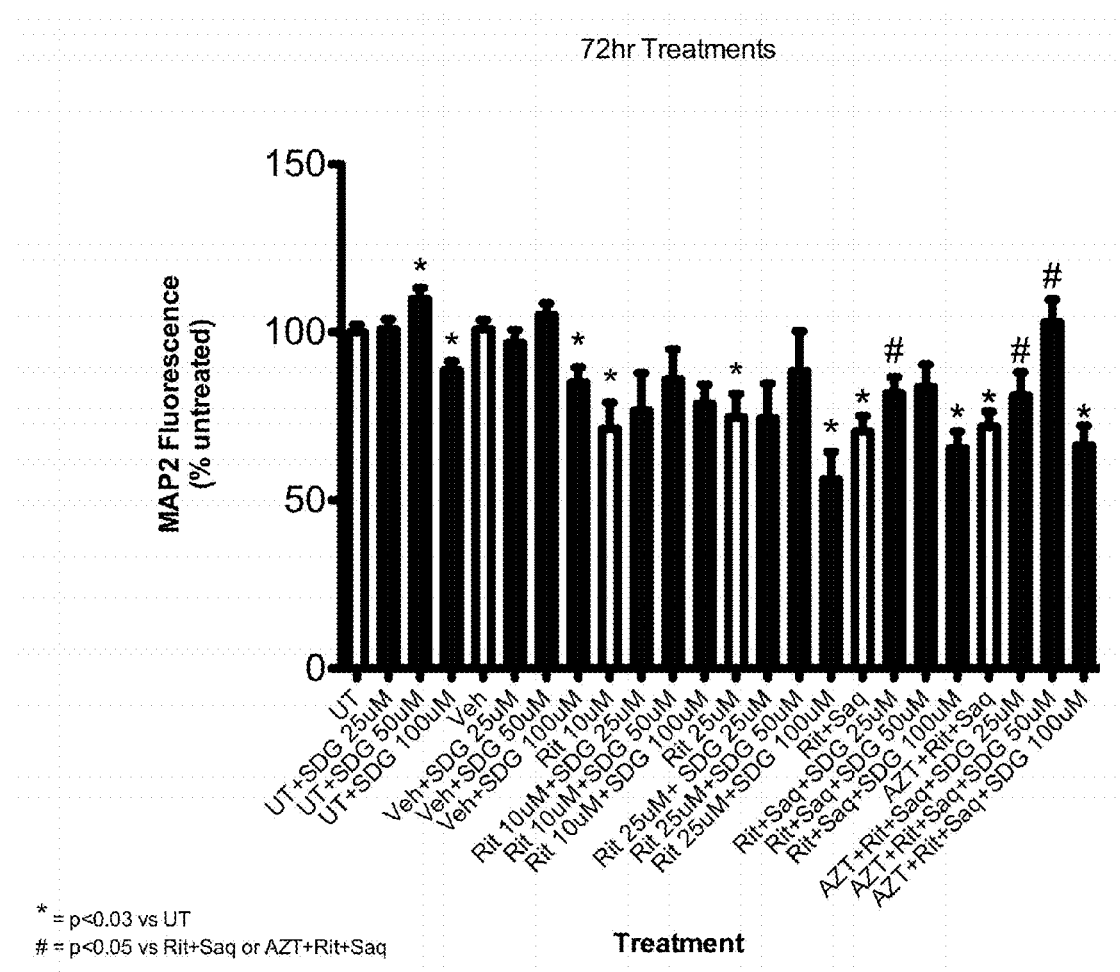
FIG. 4 shows a dose-dependent neuroprotective effect of Secoisolariciresinol Diglucoside (SDG). Relative neuronal damage as indicated by MAP2 cell-based ELISA with or without 25 μM, 50 μM or 100 μM SDG. Cells were treated for 72 hours with ritonavir (10 μM or 25 μM), ritonavir (10 μM)+Saquinivir (1 μM), AZT (25 μM)+ritonavir+Saquinavir. One hour before and two hours after cART drug treatment, half of the wells of a 96 well plate of neuroglial cultures were also treated with SDG (25 or 100 μM) where indicated. 72 hours later, a MAP2 cell-based ELISA assay was used to quantify neuronal death and damage. Untreated cultures in addition to vehicle (0.08% DMSO) treated cultures with and without SDG were used as controls. The value for untreated cultures was set to 100%, and SDG and cART treated bands are expressed as a percent change from untreated. Data represent the average±SEM counts of at least three biological replicates. *$p<0.0001$ vs UT, #$p<0.0005$ vs UT or Rit+Saq, @$p<0.005$ vs AZT+ritonavir+Saquinavir, $$p<0.05$ vs AZT+ritonavir+Saquinavir.

We have investigated the potential neurotoxic effects of several antiretroviral compounds alone and in therapeutic combinations in an acute, in vitro model of CNS toxicity. Using primary rat cortical neurons exposed to ritonavir (RIT), saquinavir (SAQ), and Zidovudine (AZT) alone and in combinations, we have observed significant neuronal damage as indicated by loss of MAP2 staining in cortical neurons (FIG. 1). Pretreatment of neurons with 25 μM of the flaxseed lignan, SDG, 1 hour prior to addition of ART compounds significantly attenuated neuronal damage in response to treatment with ART compounds alone or in combination (FIG. 3). Interestingly, SDG reduced ART-induced neuronal damage by combination therapy at 25 and 50 μM, but not at 100 μM, when the SDG alone appears to damage neurons (FIG. 4). Taken together, these findings indicate that SDG can protect neurons from damage induced by several ART compounds alone or in combination in vitro.

Example 2

HIV Replication in Peripheral Blood Mononuclear Cells (PBMCS) and MDMS in the Presence and Absence of SDG PBMCs can be prepared from laboratory donors. PBMCs are activated with 2.5 mg/mL phytohemagglutinin for 3 days, and infected with HIV-1 jago, a strain of HIV1 isolated from the CSF of a patient with HAD. On the day of infection, cultures is treated with SDG over a range of doses (0.1, 1, 10, 100 μM SDG), vehicle, or left untreated. Viral replication is assessed by p24 ELISA at 3, 6, 9, 12 and 15 days post-infection. Cell viability of infected PBMCs can be monitored by trypan blue exclusion and p24 levels are normalized to the number of viable cells. The experiment is repeated in 3 donors. MDMs can be prepared as described previously and infected with HIV-1 jago. On the day of inoculation with HIV-1 jago cultures can be treated with 0.1, 1, 10 and 100 μM SDG, vehicle or left untreated. Viral replication is assessed on days 3, 6, 9, 12, and 15 by p24

ELISA. Cell viability is determined by trypan blue exclusion and p24 levels is normalized to the number of viable cells. The experiment is replicated in 3 donors.

Results

Figure 2:
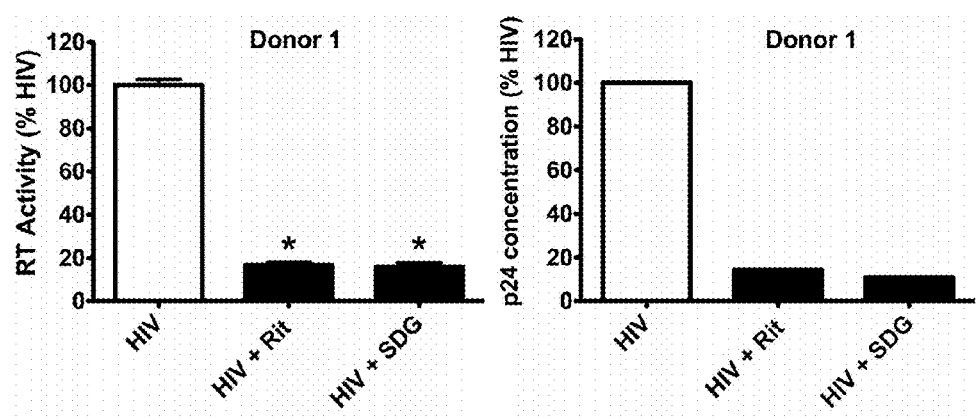
FIG. 2 shows that SDG attenuates viral replication in human monocyte-derived macrophages (MDMs). Primary human MDMs were infected with an HIV isolated from the CSF of a patient with confirmed HAND yielding robust reverse transcriptase activity (A) and p24 concentrations (B) after 9 days post-infection. Treatment with ritonavir (0.1 μM) or SDG (50 μM) attenuated viral replication as indicated by reduction in RT activity (A) and p24 concentrations (B). Results have been confirmed in 2 distinct donors, 1 donor is shown. Three technical replicates are analyzed for RT assays (n=3, * $p<0.0001$).

It is observed that SDG attenuates HIV replication in PBMCs and MDMs in a dose dependent manner. Further, treatment of HIV-infected macrophages with SDG reduced viral replication to levels akin to the HIV protease inhibitor, ritonavir (FIG. 2).

Example 3

SDG Inhibits HIV Replication in Concert with Commonly Used ARV Drugs

To determine if SDG acts synergistically or in parallel with antiretroviral (ARV) compounds; one compound from each ARV class currently in clinical use: emtricitabine (a nucleoside reverse transcriptase inhibitor), efavirenz (a non-nucleoside reverse transcriptase inhibitor), ritonavir (a HIV protease inhibitor)) and raltegravir (an integrase inhibitor) is used. PBMCs and MDMs are isolated as described previously, and infected with HIV-1 j ago. Infection occurs in the presence or absence of SDG, at a concentration determined above (Example 2), to reduce HIV replication by 50% at day 6, with the concomitant ARV being tested present in the media. For each ARV compound, SDG effects at 0.1, 0.3, 1, and 10 µM of the ARV are assessed, as well as a vehicle control. Viral replication is assessed by p24 ELISA and reverse transcriptase assays at days 3, 6, 9, 12, and 15. The experimental paradigm is repeated in 3 donors.

Example 4

Mechanism of SDG-Mediated Inhibition of HIV Replication

To inhibit viral replication MDM and HIV-infected MDM are treated with an SDG concentration determined in Example 2. At one time point post-infection where HIV replication is inhibited (i.e. day 9), nuclear and cytoplasmic protein lysates are generated from the macrophages and analyzed for 1), phosphorylation of the inhibitor of kappa B and its kinase (IKK/IkB), for 2) nuclear translocation of p65, for 3) phosphorylation of IkB inhibitory subunits (alpha, beta and epsilon), for 4) phosphorylation of p65 phosphorylation (ser276) via PKA by immunoblot. Using nuclear extracts DNA binding of NF-kB homo/heterodimers in complex with the HIV LTR is assessed by electrophoretic mobility shift assay and supershift of observed bands with p50, p65, and RelB antibodies. Alterations to the cell's oxidative state also alters NFkB activity by PKC-dependent mechanisms, and consequently, the effects of SDG on classical (alpha and beta), novel (delta) and atypical (zeta) PKC isoform activity (via selective inhibitors) are assessed. Parallel experiments are performed in PBMCs.

Example 5

Anti-Retroviral Effects of Flaxseed Lignan SDG

Materials and Methods

Figure 5A:
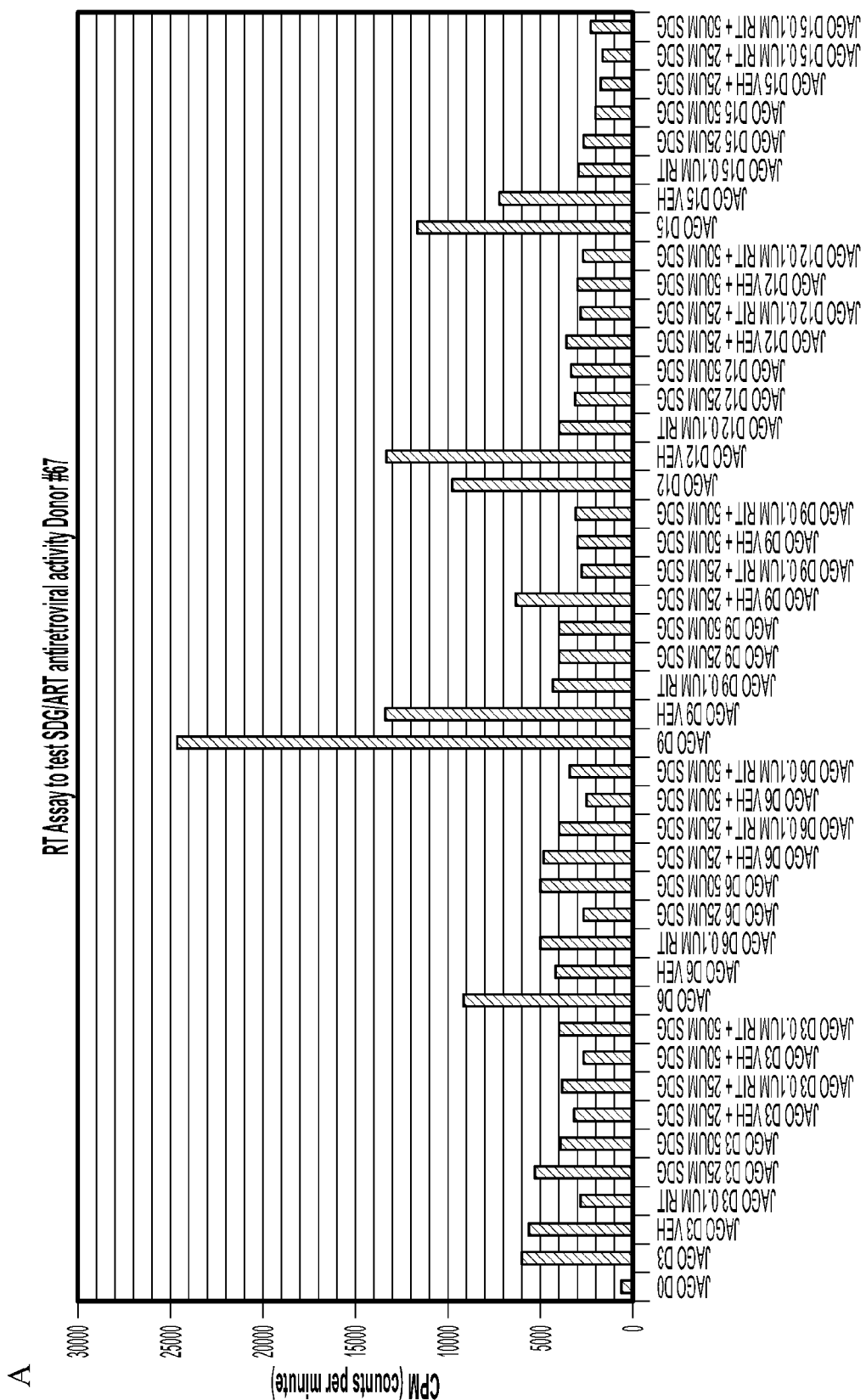
FIG. 5 (A, B) shows that Secoisolariciresinol diglucoside (SDG) does not block the ability of ritonavir to inhibit human immunodeficiency virus (HIV) replication. Monocytes from healthy donors were infected with the primary HIV isolate jago and were treated with 25 μM or 50 μM SDG, the antiretroviral compound ritonavir (0.1 μM RIT), SDG and ritonavir together, the ritonavir vehicle, DMSO, or with no additional treatment one day after infection. Supernatant from these macrophages was harvested 3, 6, 9, 12, and 15 days post infection and assayed for HIV reverse transcriptase activity.
Figure 5B:
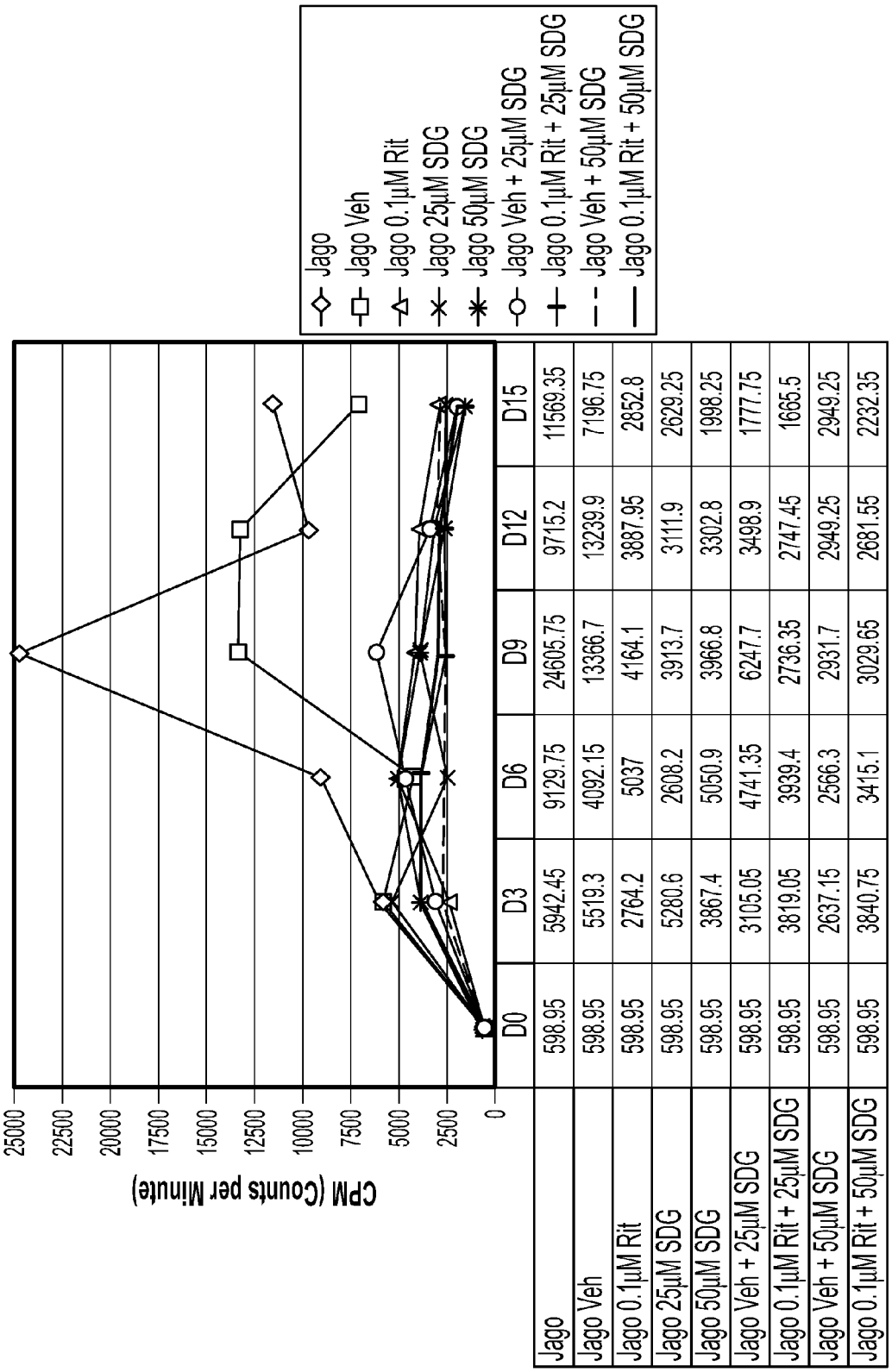

In order for SDG to be used as an adjunctive therapy, it is preferable that it does not interfere with the ability of ART compounds to inhibit HIV replication. To assess this effect, primary peripheral blood monocytes were harvested from healthy donors and differentiated them into macrophages in vitro. Monocytes were infected with the primary HIV isolate, jago. One day after infection, macrophages were treated with 25 µM or 50 µM SDG, the antiretroviral compound ritonavir (0.1 µM RIT), SDG and ritonavir together, the ritonavir vehicle, DMSO, or with no additional treatment. Supernatant from these macrophages was harvested 3, 6, 9, 12, and 15 days post infection and assayed for HIV reverse transcriptase activity (FIG. 5A, bar graph and FIG. 5B, Line graph).

Results

SDG did not block the ability of ritonavir to inhibit HIV replication. Further, SDG itself blocked HIV replication without ritonavir. These findings indicate that SDG has antiretroviral activity as well as the ability to ameliorate the neurotoxic side effects of other antiretroviral compounds.

Taken together, these findings indicate that SDG and its derivatives should be considered as adjunctive therapies to treat HIV patients as these compounds have the ability to attenuate viral replication and ART neurotoxicity. The benefits of SDG as an adjunctive therapy to HIV patients are two-fold. Its antiviral activity may reduce the need for the higher concentrations and/or combinations of antiretroviral compounds to keep HIV replication under control. Secondly, its neuroprotective activity will ameliorate ART side effects in the CNS and possibly in the PNS, liver, vasculature and heart.

Example 6

Role of Nrf2 in SDG Neuroprotection Against HIV-Induced Neurotoxicity

Figure 6:
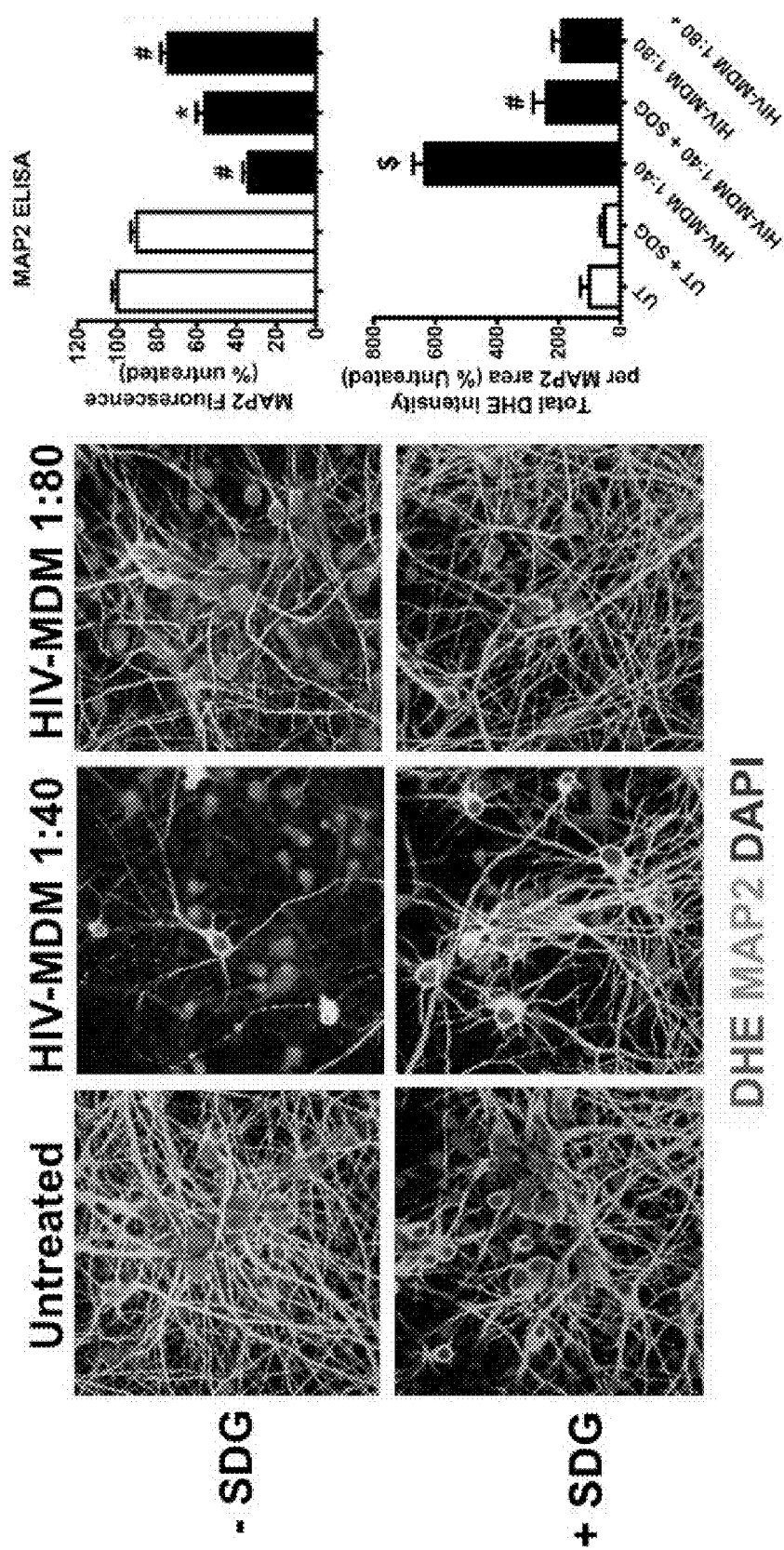
FIG. 6 shows antioxidant/neuroprotective effects of SDG in cortical rat neurons. Neurons (green) were pre-treated with 50 µM SDG 1 hour prior to exposure to HIV-infected macrophage supernatants (HIVMDM) at dilutions of 1:40 and 1:80. In the absence of SDG, there is marked reduction in MAP2 immunostaining (green) indicating neuronal damage and death (A). Labeling with dihydroethidium (red) indicates the presence of oxidative stress, which is apparent in HIVMDM treated cultures. Nuclei are labeled blue by DAPI. Treatment with SDG (lower panels) protected against neuron loss (green) and reduced accumulation of oxidative stress by DHE (RED). MAP2 levels are quantified in top graph (# $p<0.01$ compared to UT, * $p<0.05$ compared to respective HIV MDM). Oxidative stress (red-DHE) is quantified in bottom graph (# $p<0.001$, compared to HIVMDM1: 40, $p<0.05$, compared to HIVMDM1:80, \$ $p<0.01$ compared with UT.
Figure 7:
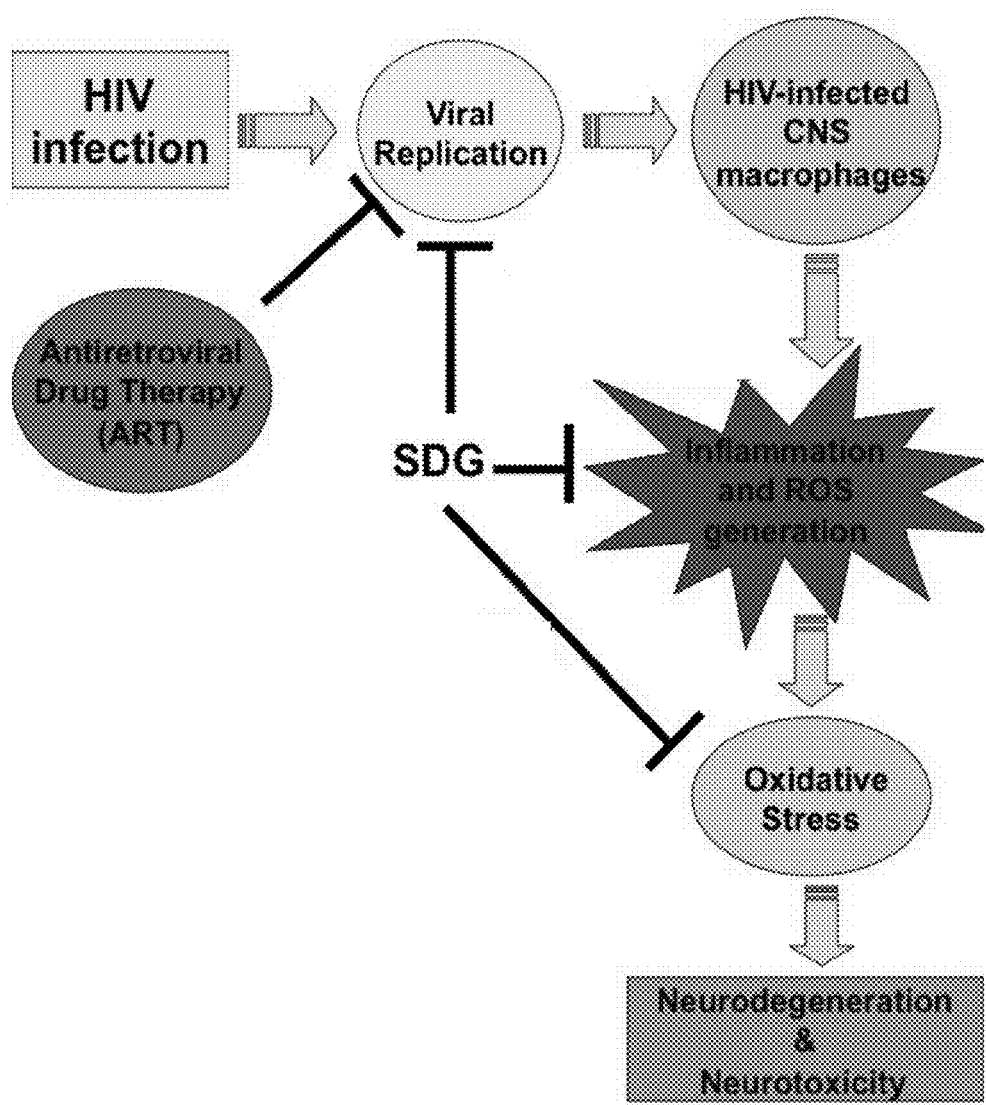
FIG. 7 schematically shows the SDG antiretroviral and neuroprotective activities in HIV infection of the CNS.

Studies indicate that SDG can provide protection against HIV-induced neurotoxicity (FIG. 6). To determine the contribution of the EAR to neuroprotection two complementary approaches are followed: 1) molecular manipulation and 2) pharmacologic inhibition of Nrf2 pathway mediators.

For molecular manipulation, the following is used: 1) wild-type neurons expressing a dominant negative Nrf2, and 2) wild-type neurons in which Nrf2 has been depleted by siRNA. Primary rat cortical cultures will be infected with an AAV-vector expressing dominant negative Nrf2, Nrf2 siRNA or the respective control backbone constructs. Cultures are then treated with HIVMDM in the presence or absence of 1, 3, 10, or 50 µM SDG, 2 days following AAV-vector infection to allow reduction in Nrf2 activity before the start of the treatment paradigm. To verify reduction in Nrf2-activity, it is ensured that HO1 and NQO1 mRNA levels, as determined by qPCR, do not increase in AAV-vector-infected cultures treated with tertbutylhydroxyperoxide (Invitrogen), a known Nrf2 inducer. Further verification of Nrf2 knockdown is done by immunoblot and realtime PCR for key targets (Nrf2, hemoxygenase 1 (HO1), NADPH quinone oxidoreductase (NQO1), Gultathione-S-Transferseu (uGST) and superoxide dismutase1 (SOD1)). These AAV-vectors were generated and their efficacy is tested in knocking down Nrf2 expression and activity in primary rat neurons (data not shown).

Infected and control primary rat cortical neurons are treated in parallel for 6, 12, or 24 hours with supernatants from HIV-infected MDM (HIVMDM) following a pretreatment with 1, 3, 10, or 50 µM SDG for 30 minutes or with no pretreatment. As controls, Mock-infected MDM supernatants are used to treat primary neurons in the presence or absence of SDG pretreatment. Neuron damage and death are assessed by MAP2 cell based ELISA, propidium iodide exclusion, and counting the numbers of MAP2 positive neurons. Mitochondrial membrane potential are measured in parallel experiments using the tetramethylrhodamine methyl ester methodology. Presence of oxidative stress is assessed by staining with dihydroethidium (DHE) incorporation. Experiments are replicated 3 times and statistical significance is determined by one way ANOVA with Neuman-Keuls ($p<0.05$).

Pharmacologic inhibitors of the key antioxidant enzymes, specifically inhibitors of HO1 (Sn(IV) mesophorphyrin IX dichloride (SnMP), 20 µM), NQO1 (dicumarol (0.01-3 µM)), and SOD1 (diethyldithiocarbamate (DETC), 1 µM) are used to assess whether SDG acts through the cellular antioxidant response in our HIVMDM-treatment paradigm. For both, molecular manipulation and use of pharmacologic inhibitors, ROS production, $\Delta\Psi_m$, and neurotoxicity is assessed as described above.

Example 7

Expression Profiles of SDG-Treated Neurons in the Presence, and the Absence of HIV-Induced Neurotoxicity To further elucidate the mechanisms of neuronal protection elicited by SDG in neurons exposed to HIVMDM, microarray analysis is performed followed by pathway analysis. Primary rat cortical neurons are treated with HIVMDM, Mock MDM or left untreated for 6 or 24 hours in the presence or absence of a concentration of SDG that provides significant neuroprotection. RNA is extracted for microarray analysis using the RatRef-12 Expression Bead-Chip Kit (Illumina) performed by the Wistar Institute Genomics Facility. Pathway analysis is performed by the Wistar Institute Genomics Facility, as previously described. Once the pathways are identified, key transcription factors found modulated in the gene expression analyses, are identified for future investigation. Validation is provided by protein analyses and gene knockdown by siRNA and/or pharmacological inhibitors that target genes in the modulated pathways. Experiments are repeated 3 times and statistical significance determined by two way ANOVA with Neuman-Keuls ($p<0.05$). To assess the significant differences between groups in the microarray analysis, a >1.5-fold change filter and permutation based t-test ($p<0.05$) are performed using the TIGR Multi Experiment Viewer. In addition, the genes that are regulated by SDG in the brain are identified for comparison with our gene array in primary neuronal cultures. To this end, parallel experiments are performed on brain RNA from rats given SDG via oral gavage. A picture of which pathways are engaged in neurons responding to HIV infected MDM, and which mediate SDG neuroprotection will suggest additional pharmacologic interventions targeting these pathways.

Example 8

Orally Administered SDG Crosses the Blood-Brain Barrier and Induces Nrf2-Regulated Antioxidant/Protective Enzymes in Mice Brain Tissues Ma and coworkers (*Antidepressant-like effect of flaxseed secoisolariciresinol diglycoside in ovariectomized mice subjected to unpredictable chronic stress*. Metab Brain Dis, 2013. 28(1): p. 77-84.) have shown that SDG given by oral gavage decreased chronic stress as measured by immobility time induced by tail suspension stress in mice. This was associated with an increase in cortex levels of brain derived neurotrophic factor (BDNF), an indication that orally-administrated SDG affects gene expression in brain tissues. Demonstrating that SDG crosses the blood-brain barrier and that SDG is located at a location where HIV-infected macrophages are present and where SDG can exert CNS protection in HIV-infected patients.

Mice received consecutive oral gavages of 0.1, 0.5 and 1.0 mg SDG once daily for 4 days and were sacrificed 4 hours post the final feeding. Brain tissues were isolated and processed for qRT-PCR to detect gene expression levels of nrf2-regulated protective enzymes belonging to the tissues' endogenous antioxidant response (EAR).

Figure 8:
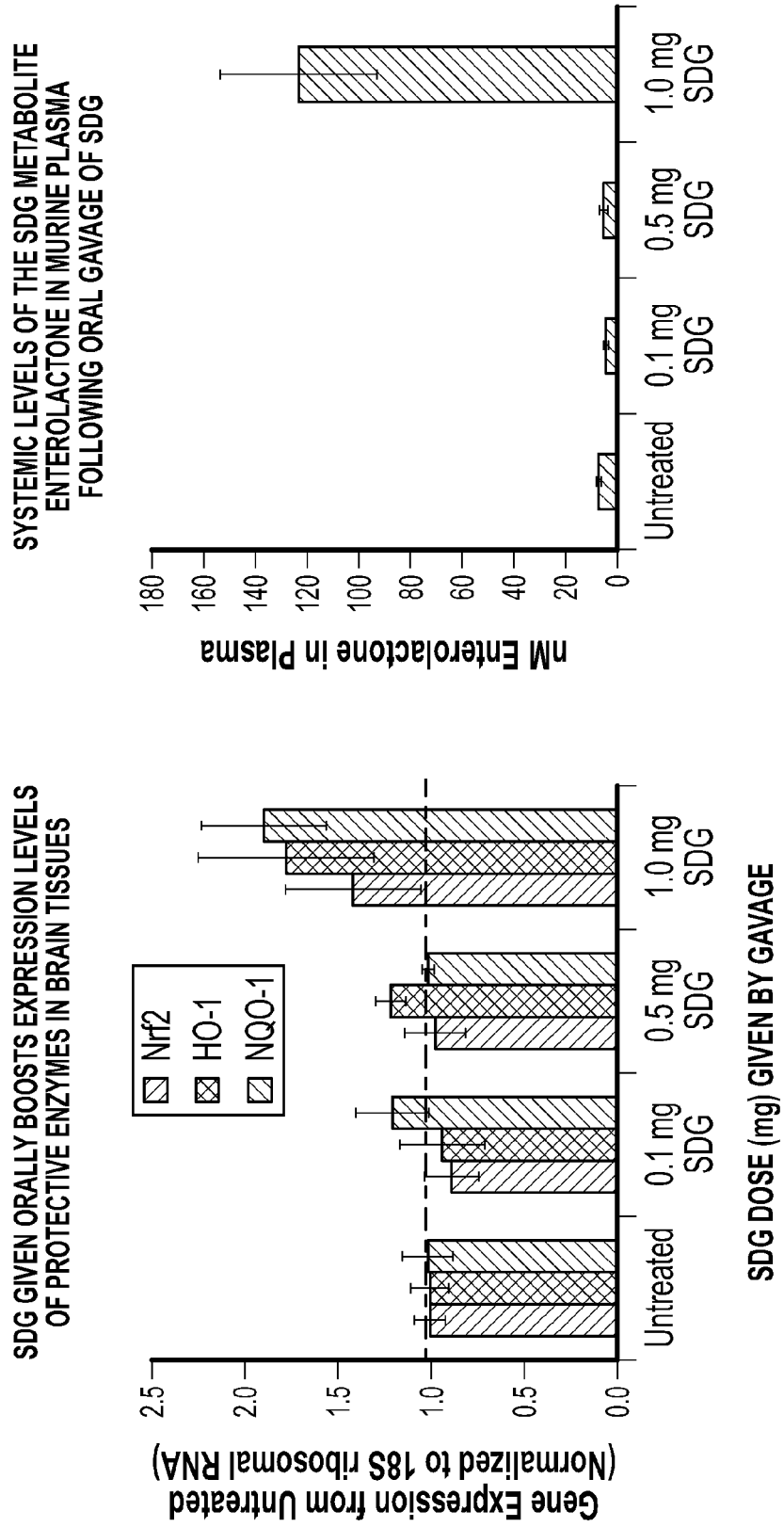
FIG. 8 (left panel) Antioxidant enzyme gene expression levels in murine brain tissues after SDG ingestion. (right panel) Plasma levels of the lignan metabolite enterolactone (EL) determined by mass spectrometry and gas chromatography (GC/MS/MS).

Indeed, the 1.0 mg dose was associated with a near 2-fold boost of hemeoxygenase 1 expression (HO-1) and quinone oxidoreductase 1 (NQO-1) expression in brain tissues (FIG. 8, left panel). These are representative antioxidant and tissue protective enzymes Importantly, the 1 mg dose of orally-administered SDG that was associated with the most robust increase in protective enzyme gene level increases, also showed detectable systemic levels of SDG metabolites such as enterolactone (EL) shown in (FIG. 8, right panel). This data shows that orally given SDG affects gene expression levels of protective enzymes in the brain, and were associated with systemic levels of SDG metabolites. This in vivo finding demonstrates that protective mechanisms are induced in the brain by dietary supplementation of this flaxseed lignan.

Example 9

Figure 9:
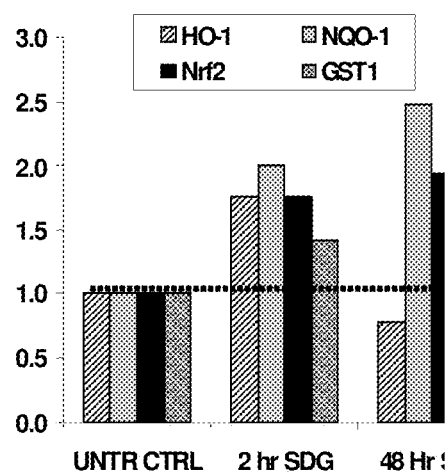
FIG. 9 shows the kinetics of Nrf2 regulated gene expression in neuronal cells exposed to 50 µM SDG.

SDG Induces Nrf2 and the Endogenous Antioxidant Response (Ear) in Primary Cortical Rat Neurons In vitro studies have demonstrated that the flaxseed lignan phenolic, SDG induces Nrf2 and the endogenous antioxidant response (EAR) in primary cortical rat neurons (FIG. 9). Specifically, protein and RNA from primary rat cortical neurons treated with SDG at 50 µM or left untreated for 2 or 48 hours were analyzed for changes in expression of the endogenous antioxidant response by qRT-PCR and immunoblot. We found that SDG induced Nrf2, as well as its prominent targets: HO1, NQO1, and GST1 (FIG. 9).

Example 10

SDG Protects Neurons from HIV-Stimulated Macrophage-Induced Neurotoxicity in the Presence or Absence of Glia Primary rat neuroglial cultures (FIG. 10, Panel A) and primary rat neuronal cultures (FIG. 10, Panel B) were treated with Supernatants from HIV-Infected macrophages (Jago) or Mock-infected macrophages (Mock) for 24 hours in the presence or absence of 25 or 50 µM SDG given 60 minutes prior to addition of the HIVMDM. Prior to fixation, cells were incubated with Dihydroethidium (DHE-red) for 30 minutes. Following fixation cells were stained for the neuronal specific marker MAP2 (green) and DAPI (blue). Representative images for each treatment are shown. DHE Fluorescence intensity was quantified from 6 fields for 3 slides per treatment, averaged, and normalized to the area of DAPI. Graphs of the average DHE staining intensity/DAPI area are plotted for each treatment group. The p values were generated using student's two-tailed t-test for equal variance. Bars on graphs represent median values of quantification by ImageJ algorithm. *$P<0.05$ vs Untreated (UT)-control group and Mock-control group; #$P<0.05$ vs Jago 1:40 treatment group. The results were obtained from at least three independent experiments.

The results clearly show that SDG protects neurons from HIV-stimulated macrophage-induced neurotoxicity in the presence or absence of glia.

Example 11

SDG Reduces Free Radical Formation in HIV-Jago Treated Neurons

Figure 10B:
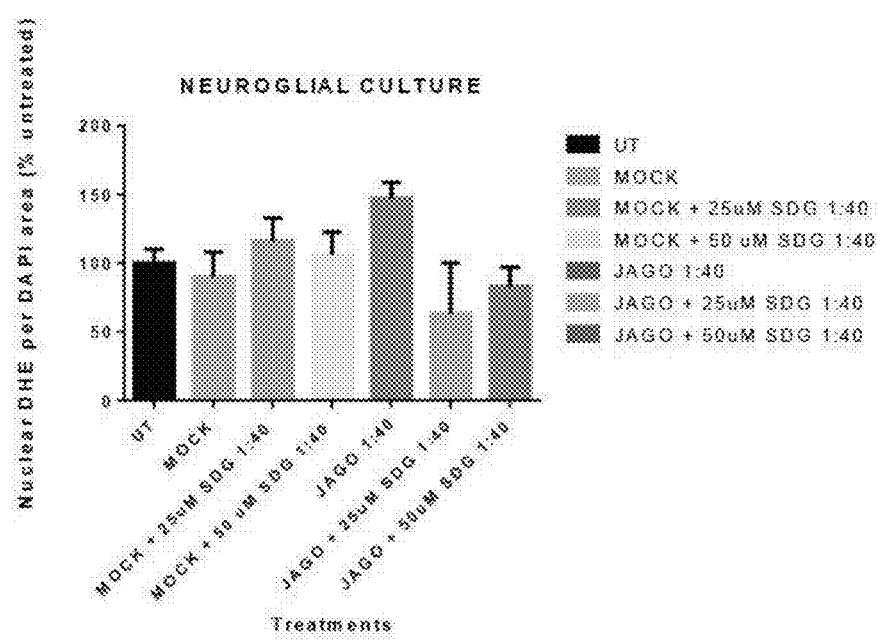
FIG. 10 (A-1 to A-28, B) shows that the lignan SDG protects neurons from HIV-stimulated macrophage-induced neurotoxicity in the presence or absence of glia cells.
Figure 10D:
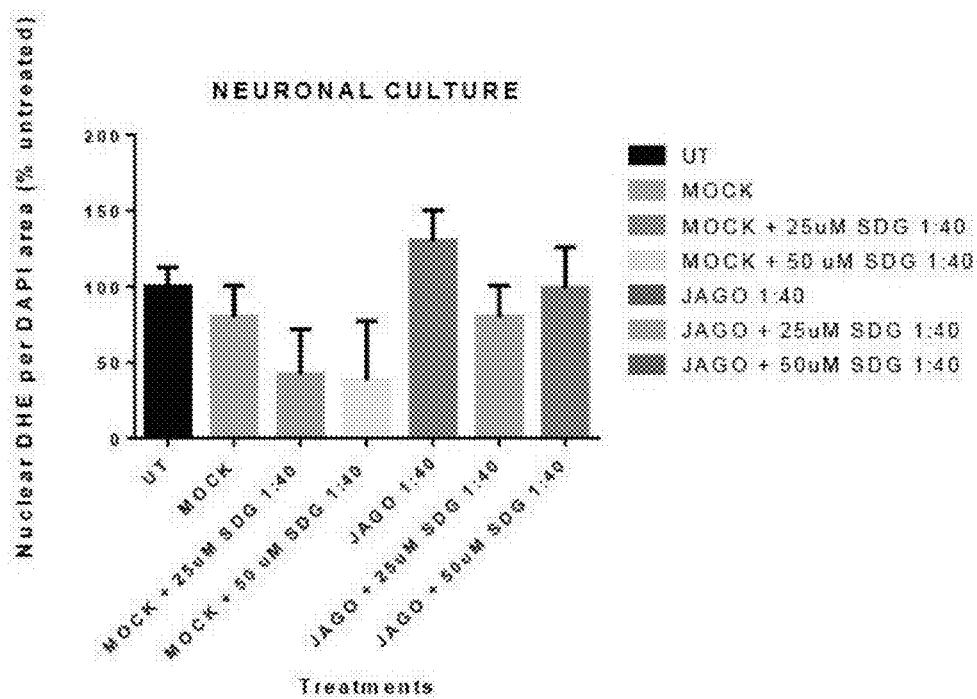
Figure 11:
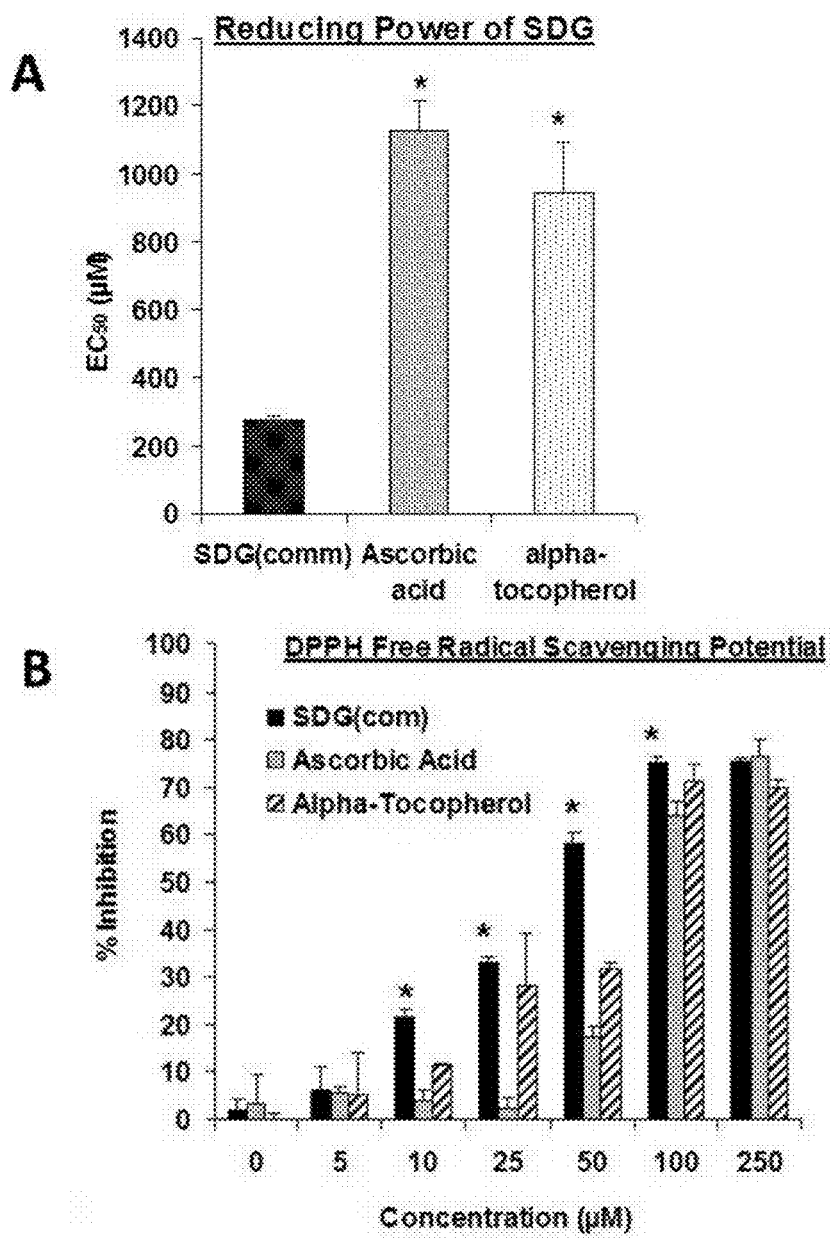
FIG. 11 shows that SDG is a potent antioxidant agent, more robust than other natural antioxidant agents such as ascorbic acid (Vitamin C) and tocopherol (Vitamin E).

As shown in FIG. 10, Panels A and B, treatment of primary rat neurons with HIV-Jago, in the presence of absence of glia, resulted in increased DHE intensity per nuclei indicating an increase in free radical production. Also, as shown in FIG. 10, Panels A and B, treatment with SDG reduced DHE staining in HIV-Jago-treated neurons in the presence and absence of glia.

These data clearly show that SDG reduces free radical formation in neurons treated with HIV-Jago.

Example 12

SDG is a Potent Antioxidant

The antioxidant activity SDG was determined by assessing its reducing power, an activity related to its ability to reduce an oxidized atom or molecule and compared with that of the natural antioxidants ascorbic acid and alpha-tocopherol (Panel A). The data show a nearly 3-fold higher concentration of A-toc and AA is needed as compared to SDG to achieve the half-maximal response for each agent ($EC_{50}$).

Similarly, the DPPH free radical scavenging activity of the 3 agents was determined and results indicated a far superior antioxidant activity of SDG as compared to the other, known antioxidants (Panel B).

Example 13

Figure 12A:
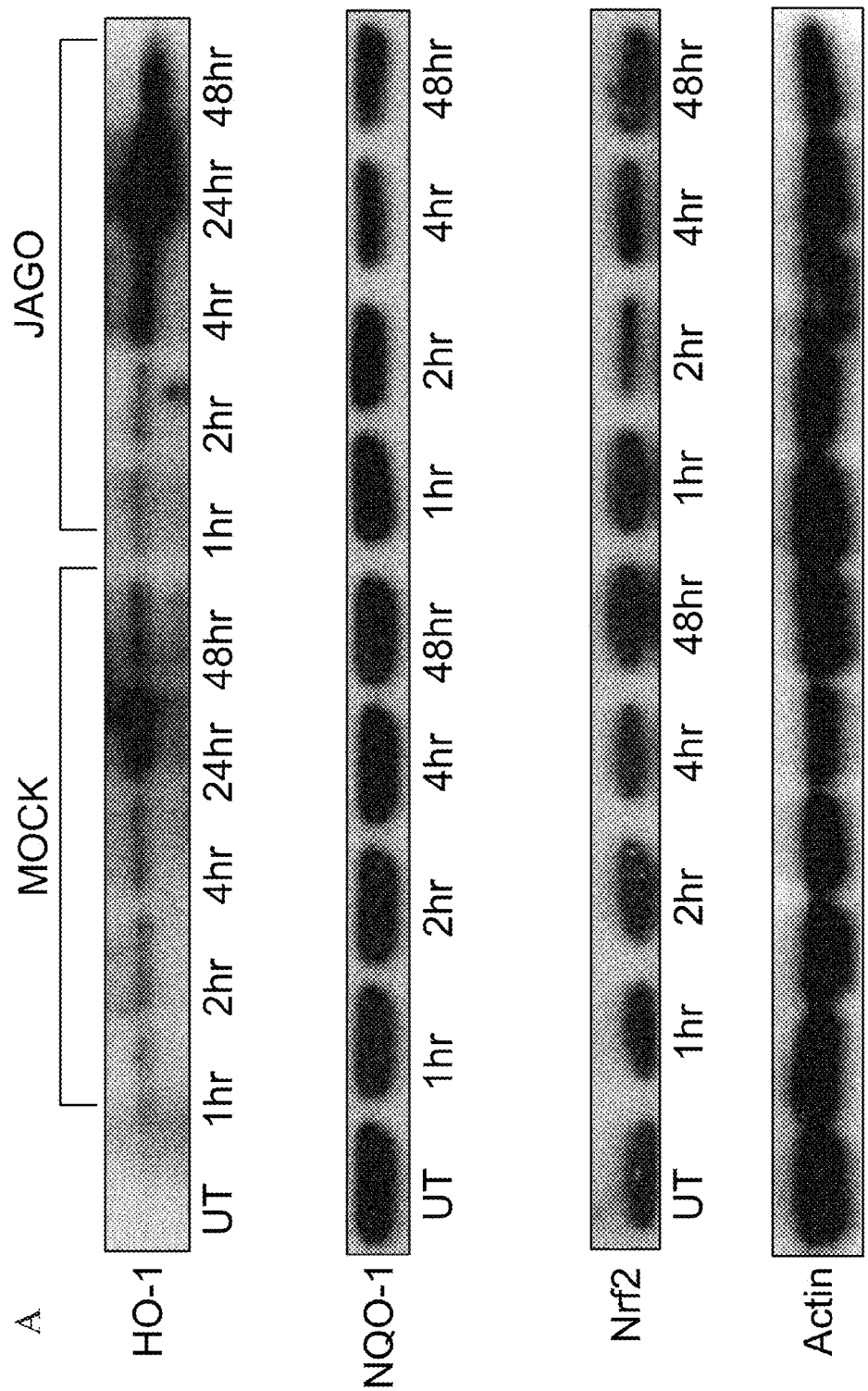
FIG. 12 (A, B-1 to B-3) shows that HIV infected monocyte-derived macrophages (MDM) supernatants modulate the endogenous antioxidant response element (ARE) pathway in primary cortical cultures.

HIV-Infected MDM Supernatants Modulate the Endogenous Antioxidant Response Element (are) Pathway in Primary Cortical Cultures Rat cerebrocortical cultures were exposed to supernatant from uninfected (MOCK) and HIV-infected macrophages for 1, 2, 4, 24 and 48 hrs and protein expression of ARE markers such as HO-1, NQO1 and Nrf2 were assessed by Western blotting (FIG. 12, Panel A) and quantified by densitometry analysis (FIG. 12, Panel B).

This data show that HIV infected MDM supernatants induce a rapid but transient increase in HO-1 expression in primary rat cortical cultures.

Example 14

Figure 13:
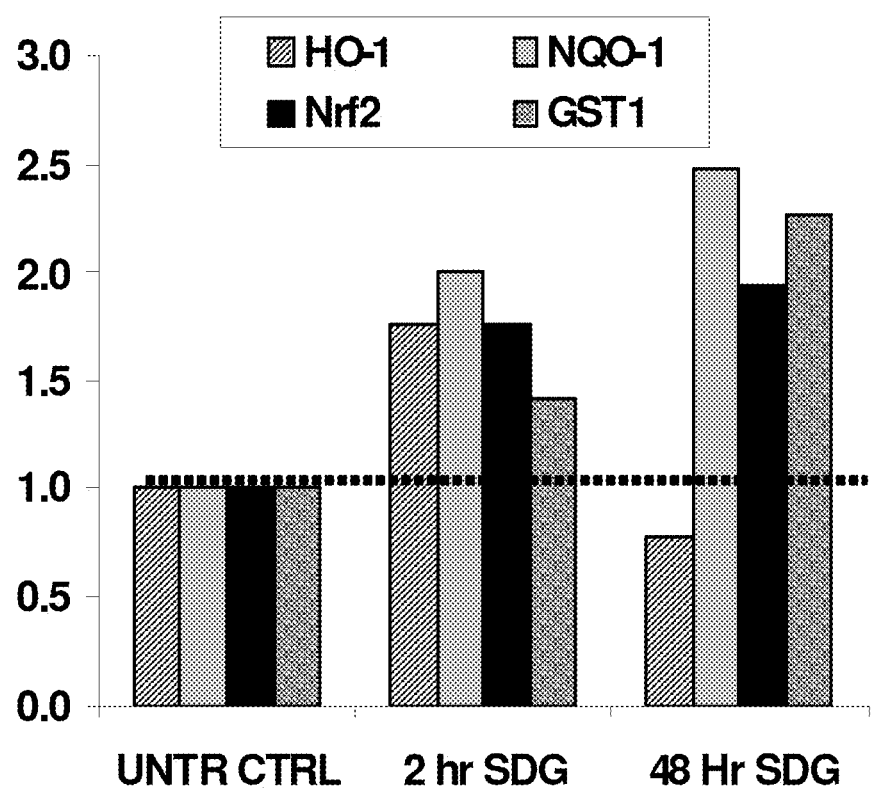
FIG. 13 shows that SDG induces protective enzymes in neuronal cells.

SDG Induces Nrf2 and the Endogenous Antioxidant Response (Ear) Pathway in Primary Cortical Rat Neurons As shown in FIG. 13, our results show that SDG activates the Nrf2/ARE in non-neuronal cell types such as lung epithelial, endothelial and fibroblasts, inducing NADPH quinone oxidoreductase (NQO1) and heme oxygenase 1 (HO1). Protein and RNA from primary rat cortical neurons treated with SDG at 50 μM or left untreated for 2 or 48 hours were analyzed for changes in expression of the endogenous antioxidant response by qRT-PCR and immunoblot.

We found that SDG induced Nrf2 in neurons, as well as its prominent targets: HO1, NQO1, and GST1.

Example 15

Figure 14:
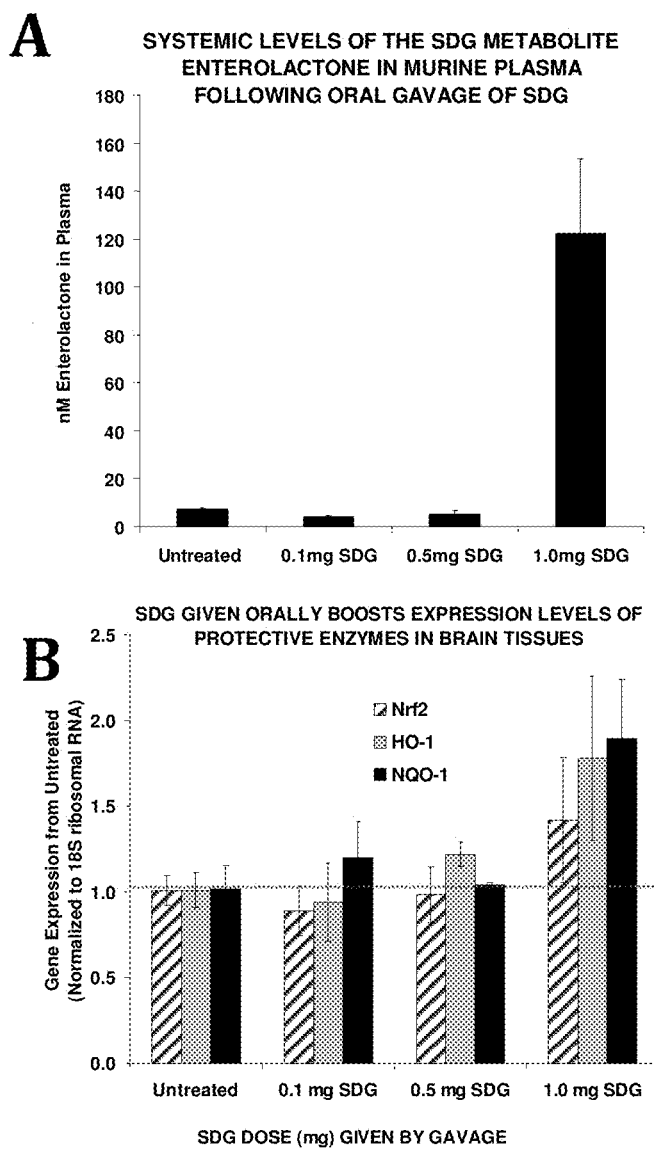
FIG. 14 shows that SDG given orally to mice crosses the blood-brain barrier and affects endogenous antioxidant brain defenses by boosting expression of protective enzymes.

SDG Given Orally to Mice Induces Nrf2 and the Endogenous Antioxidant Response (Ear) Pathway in Brain Tissues As shown in FIG. 14, mice received consecutive oral gavages of 0.1, 0.5 and 1.0 mg SDG once daily for 4 days and sacrificed 4 hours post the final feeding. Brain tissues were isolated and processed for qRT-PCR to detect gene expression levels of nrf2-regulated protective enzymes belonging to the tissues' endogenous antioxidant response (EAR). Indeed, the 1.0 mg dose was associated with a near 2-fold boost of hemeoxygenase 1 expression (HO-1) and quinone oxidoreductase 1 (NQO-1) expression in brain tissues (FIG. 14, Panel B). These are representative antioxidant and tissue protective enzymes Importantly, the 1 mg dose of orally-administered SDG that was associated with the most robust increase in protective enzyme gene level increases, also showed detectable systemic levels of SDG metabolites such as enterolactone (EL) shown in (FIG. 14, Panel A). This data show that orally given SDG affects gene expression levels of protective enzymes in the brain, associated with systemic levels of SDG metabolites. This finding demonstrates that protective mechanisms are induced in brain by dietary supplementation of this flaxseed lignan.

Example 16

Indirect Treatment of SDG Resulted in No Change in Neuronal Cell Viability

Figure 15:
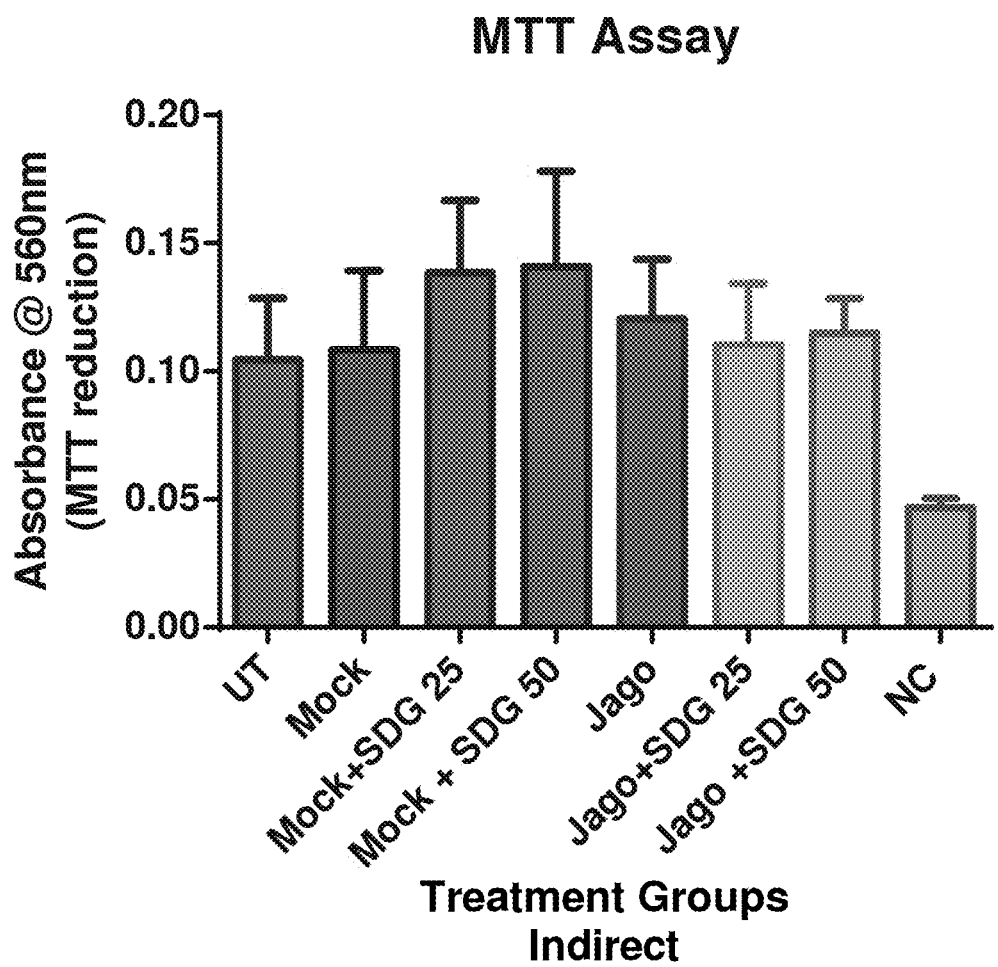
FIGS. 15 and 16 show that indirect and direct treatment of neuronal cells with SDG is not toxic, an indication for lack of cytotoxicity by SDG in neurons.

As shown in FIG. 15, indirect treatment of SDG resulted in no change in neuronal cell viability. We performed a MTT (3-(4,5-dimethylthiazol-2-yl)-2,5-diphenyltetrazolium bromide) assay to measure the viability of cells through the production of insoluble formazan. 2-4 by respiration. In these indirect studies media from HIV-1 infected or Mock infected macrophages treated with SDG was applied to neuronal cultures for 24 hours. Afterward cell viability was determined by the MTT assay which fluoresces and is an indicator of mitochondrial activity. FIG. 10 clearly shows that the co-incubation of HIV-1 and Mock infected macrophage media with rat neuronal cultures did not induce cellular death at the 24 hour time point. This study is a clear indicator of the non-neurotoxic effects of SDG in vitro. Although at this time point, neuronal death was not decreased in neuronal cultures co-incubated with HIV-1 infected and Mock infected macrophages treated with SDG, it does not exclude the production of reactive oxygen species.

Example 17

Direct Treatment of SDG Resulted in No Change in Neuronal Cell Viability

Figure 16:
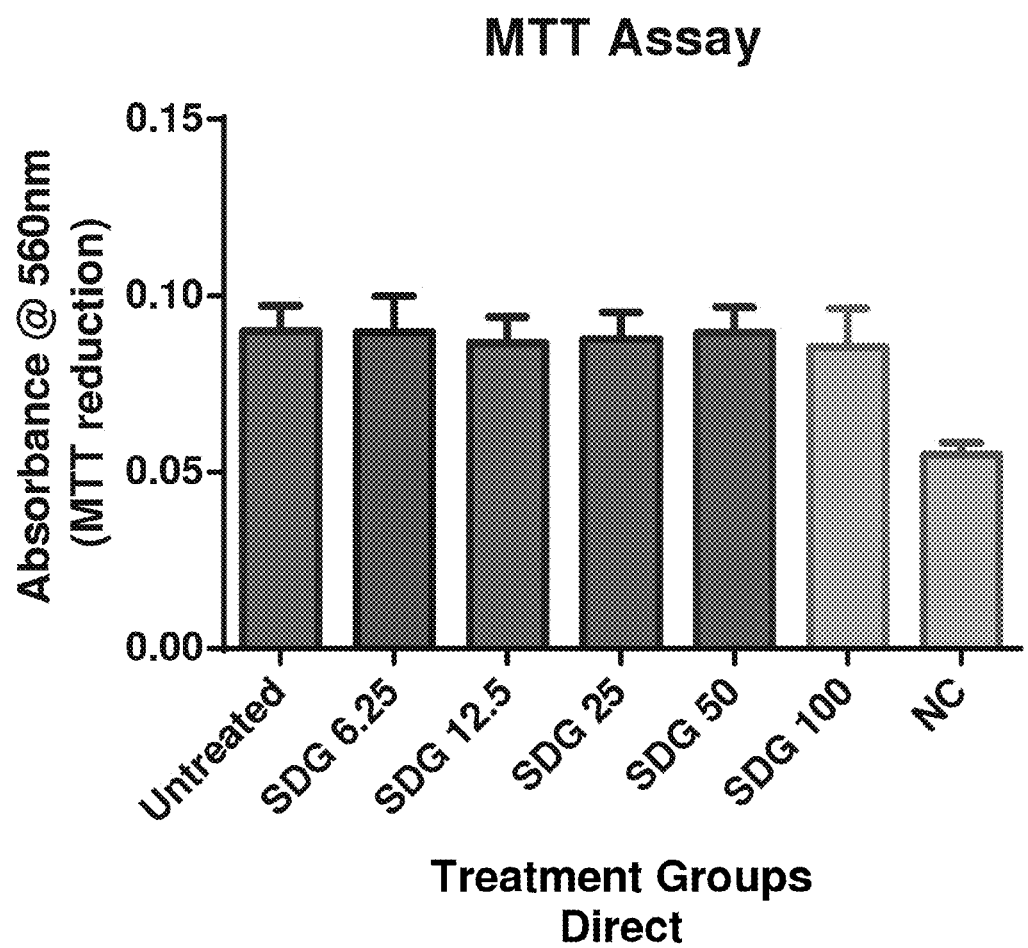

In order to assess the effects on SDG in terms of mitochondrial respiration as an indicator of viability, an MTT assay was performed with rat cortical neuroglial cultures that were treated for 24 hours with SDG. As shown in FIG. 16, after the 24 hour incubation period there was no difference in the fluorescence emitted from any of the treatment groups. Although SDG did not enhance the viability of the neuronal cultures, it is promising that they even the highest concentration of the drug did not have a cytotoxic effect after 24 hours. In sum, our results show that direct treatment of SDG resulted in no change in neuronal cell viability.

Example 18

SDG Downregulates the Expression of HIV Coreceptors CCR5 and CXCR4

The objective of this study was to elucidate the modulatory effects of flaxseed lignans on macrophage expression of coreceptors through western blotting. Our findings show that flaxseed lignans effectively decrease coreceptor expression levels in a dose-dependent manner and that the treatment was not neurotoxic.

Figure 17:
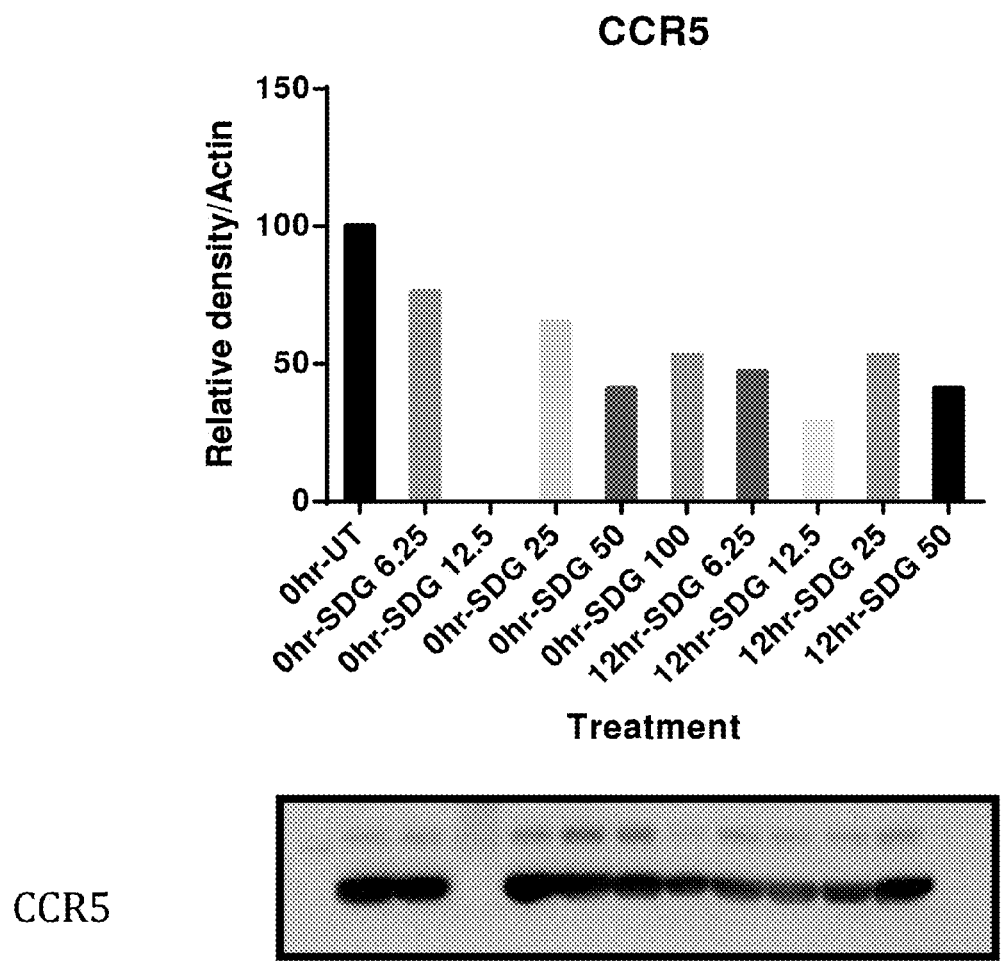
FIGS. 17 and 18 show that SDG down-regulates key receptors on macrophage cells needed for HIV entry into cells and infection.

As shown in FIG. 17, SDG downregulates expression of CCR5 on MDM. Expression of HIV co-receptor CCR5 on macrophage derived monocytes treated with SDG was evaluated. Following the same treatment protocol, MDM were treated with SDG for 0 and 6 hours. The data clearly demonstrates that SDG induces a significant decrease in the HIV co-receptor CCR5 expression in a time-dependent manner.

Figure 18:
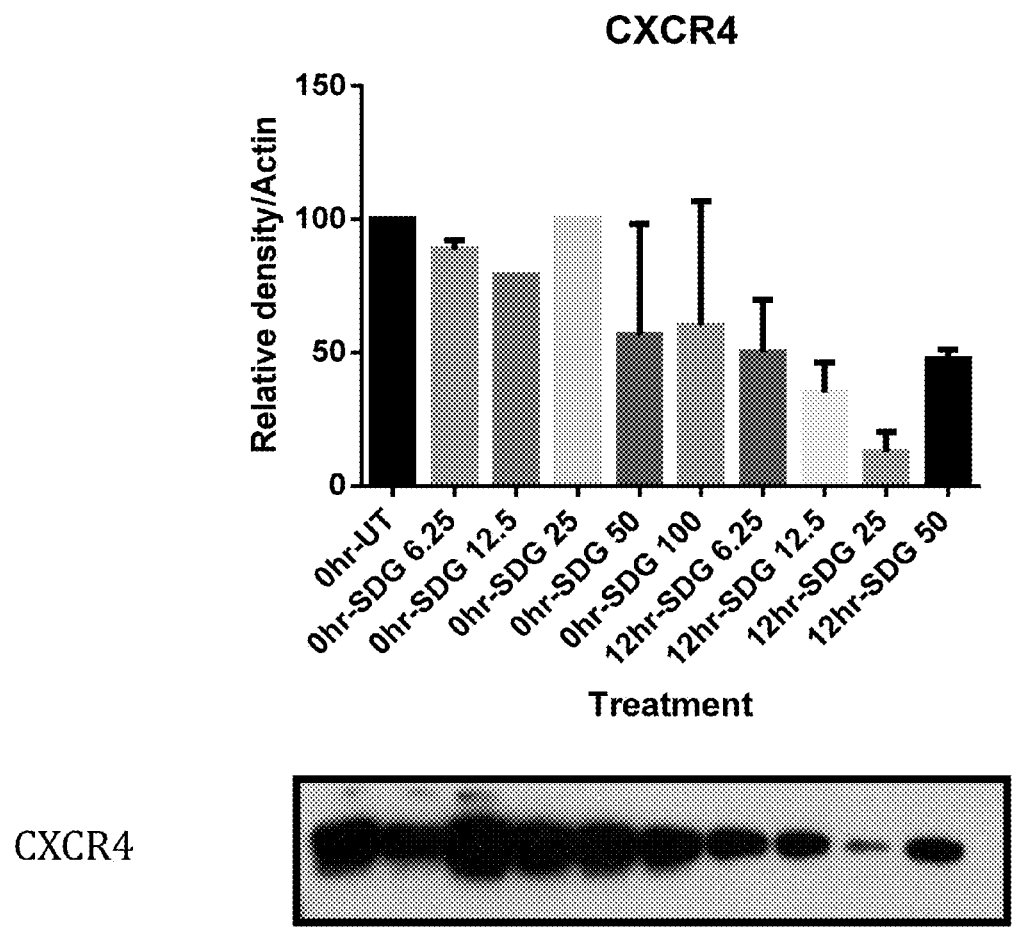

As shown in FIG. 18, SDG down-regulates expression of the HIV co-receptor CXCR4 on MDMs. Expression of HIV coreceptor CXCR4 on macrophage derived monocytes treated with SDG was evaluated. Following the same treatment protocol, MDM were treated with SDG for 0 and 6 hours. After the 0 and 6 hour incubation period there was a significant decrease in the HIV coreceptor CXCR4 expression in a time-dependent manner between the 0 and 6 hour time points. Also there was a dose-dependent decrease at the 12 hour time point from the 6. 25 µM to the 25 µM SDG treatment. Interestingly this dose-dependent decrease was observed in the 50 µM SDG treatment although the expression at this concentration was significantly lower than at the same concentration 6 hours earlier.

In sum, our results demonstrate that the flaxseed lignan attenuates macrophage protein expression of CCR5 and CXCR4 coreceptors, which are vital to HIV entry into macrophages. SDG's effect on these critical coreceptors establishes that this agent can also be used for novel therapies designed to effectively reduce HIV neuroinflammation and mitigate HIV-associated neurocognitive disorders.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for treating infection-mediated neuronal damage in a subject having infection-mediated neuronal damage comprising the step of administering to said subject a therapeutically effective amount of a lignan, wherein said lignan is a flaxseed lignan selected from the group consisting of a flaxseed lignan complex (FLC) and secoisolariciresinol diglucoside (SDG).

2. The method of claim 1, wherein said lignan is administered in the form of a flaxseed lignan complex (FLC).

3. The method of claim 1, wherein said lignan is a flaxseed lignan and said flaxseed lignan is secoisolariciresinol diglucoside (SDG).

4. The method of claim 1, wherein said step of administering comprises oral administration.

5. The method of claim 1, wherein said infection is a viral infection or a bacterial infection.

6. The method of claim 5, wherein said subject is a human and said infection is human immunodeficiency virus (HIV) infection.

7. The method of claim 6, wherein said subject is receiving antiretroviral therapy.

8. The method of claim 6, wherein said subject is diagnosed with HIV-associated Neurocognitive Disorder (HAND).

* * * * *

UNITED STATES PATENT AND TRADEMARK OFFICE
CERTIFICATE OF CORRECTION

PATENT NO. : 9,987,321 B2
APPLICATION NO. : 14/083804
DATED : June 5, 2018
INVENTOR(S) : Melpo Christofidou-Solomidou et al.

Page 1 of 1

It is certified that error appears in the above-identified patent and that said Letters Patent is hereby corrected as shown below:

In Column 1, Line 13, please insert the following:
--GOVERNMENT INTEREST STATEMENT
This invention was made with government support under grant numbers NS056885 and MH083517 awarded by the National Institutes of Health. The government has certain rights in the invention.--

Signed and Sealed this
Twelfth Day of February, 2019

Andrei Iancu
*Director of the United States Patent and Trademark Office*